United States Patent
Degani et al.

(10) Patent No.: US 8,509,570 B2
(45) Date of Patent: Aug. 13, 2013

(54) METHOD AND APPARATUS FOR COMPUTER-AIDED DIAGNOSIS OF CANCER AND PRODUCT

(75) Inventors: Hadassa Degani, Rehovot (IL); Erez Eyal, Nes-ziona (IL)

(73) Assignee: Yeda Research & Development Co. Ltd., Rehovot (IL)

( * ) Notice: Subject to any disclaimer, the term of this patent is extended or adjusted under 35 U.S.C. 154(b) by 690 days.

(21) Appl. No.: 12/598,801

(22) PCT Filed: May 16, 2008

(86) PCT No.: PCT/US2008/063936
§ 371 (c)(1),
(2), (4) Date: Nov. 4, 2009

(87) PCT Pub. No.: WO2008/144539
PCT Pub. Date: Nov. 27, 2008

(65) Prior Publication Data
US 2010/0142786 A1 Jun. 10, 2010

Related U.S. Application Data

(60) Provisional application No. 60/938,626, filed on May 17, 2007, provisional application No. 61/029,072, filed on Feb. 15, 2008.

(51) Int. Cl.
*G06K 9/60* (2006.01)

(52) U.S. Cl.
USPC ............ 382/305; 382/254; 382/132; 382/190

(58) Field of Classification Search
None
See application file for complete search history.

(56) References Cited

U.S. PATENT DOCUMENTS

| | | |
|---|---|---|
| 5,983,251 A | 11/1999 | Martens et al. |
| 6,353,803 B1 | 3/2002 | Degani |
| 6,553,327 B2 | 4/2003 | Degani |
| 6,611,778 B2 | 8/2003 | Degani |
| 6,625,303 B1 * | 9/2003 | Young et al. .................. 382/132 |

(Continued)

OTHER PUBLICATIONS

Martel et al (Assessment of brain perfusion using parametric and factor images extracted from dynamic contrast-enhanced MR images. SPIE Feb. 1998.).*

(Continued)

*Primary Examiner* — Tsung-Yin Tsai
(74) *Attorney, Agent, or Firm* — Martin Fleit; Paul D. Bianco; Fleit Gibbons Gutman Bongini & Bianco PL

(57) ABSTRACT

Method and apparatus performing dynamic contrast-enhanced-magnetic resonance imaging on tissue to obtain a plurality of datasets of images. Principal component analysis is performed on each dataset to obtain a covariance matrix and its corresponding eigenvalues and eigenvectors and produce a common base of eigenvectors. The dominant eigenvectors that are not associated with instrumental and random noise, commonly the $2^{nd}$ eigen-state and the $3^{rd}$ eigenvectors, or the $1^{st}$ and $2^{nd}$ eigen vectors, are correlated with the physiological relevant parameters of the 3TP method to obtain a hybrid method. The fusion of the eigenvectors with the 3TP parameters is dictating a rotation of the two relevant eigenvectors to obtain new rotated eigenvectors that serve to calculate new projection coefficient maps of the rotated eigenvectors for the imaged tissue indicative of physiological relevant parameters reflecting wash-out and wash-in patterns that detect abnormal tissue and distinguishes between cancerous and benign tumors. Computer-readable medium containing program instructions for carrying out the above.

8 Claims, 17 Drawing Sheets

(56) References Cited

U.S. PATENT DOCUMENTS

| | | | |
|---|---|---|---|
| 7,110,903 | B2 | 9/2006 | Degani |
| 7,184,814 | B2 | 2/2007 | Lang et al. |
| 2002/0114530 | A1* | 8/2002 | Duarte ............................ 382/254 |
| 2004/0252870 | A1 | 12/2004 | Reeves et al. |
| 2004/0264744 | A1 | 12/2004 | Zhang |
| 2004/0264755 | A1 | 12/2004 | Sakaida |
| 2005/0286768 | A1* | 12/2005 | Battle ............................. 382/190 |
| 2008/0021502 | A1* | 1/2008 | Imielinska et al. ............... 607/1 |

OTHER PUBLICATIONS

Written Opinion, published Nov. 17, 2009, for PCT/US2008/063936, filed May 16, 2008.

International Preliminary Report on Patentability, published Nov. 17, 2009, for PCT/US2008/063936, filed May 16, 2008.

Kuhl, C. "The current status of breast MR imaging. Part I. Choice of technique, image interpretation, diagnostic accuracy, and transfer to clinical practice" Radiology 244,356-378 (2007).

Twellmann, T., Saalbach, A., Gerstung, O., Leach, M. O., and Nattkemper, T. W. "Image fusion for dynamic contrast enhanced magnetic resonance imaging" Biomed Eng Online 3, 35 (2004).

Furman-Haran, E., Grobgeld, D., Margalit, R., and Degani, H. "Response of MCF7 human breast cancer to tamoxifen: evaluation by the three-time-point, contrast-enhanced magnetic resonance imaging method" Clin Cancer Res 4, 2299-2304 (1998).

International Search Report, published Jan. 15, 2009, for PCT/US2008/063936, filed May 16, 2008.

Kety, S. S. Measurement of local contribution within the brain by means of inert, diffusible tracers; examination of the theory, assumptions and possible sources of error. Acta Neurol Scand Suppl, 14: 20-23, 1965.

Kety, S. S. Observations on the validity of a two compartmental model of the cerebral circulation. Acta Neurol Scand Suppl, 14: 85-87, 1965.

Choyke, P. L., Dwyer, A. J., and Knopp, M. V. Functional tumor imaging with dynamic contrast-enhanced magnetic resonance imaging. J Magn Reson Imaging, 17, 509-520, 2003.

Collins, D. J. and Padhani, A. R. Dynamic magnetic resonance imaging of tumor perfusion. Approaches and biomedical challenges. IEEE Eng Med Biol Mag, 23(1): 65-83, 2004.

Kuhl, C. K., Mielcareck, P., Klaschik, S., Leutner, C, Wardelmann, E., Gieseke, J., and Schild, H. H. Dynamic breast MR imaging: are signal intensity time course data useful for differential diagnosis of enhancing lesions? Radiology, 211: 101-110, 1999.

Schaefer, J. F., Vollmar, J., Schick, F., Vonthein, R., Seemann, M. D., Aebert, H., Dierkesmann, R., Friedel, G., and Claussen, C. D. Solitary pulmonary nodules: dynamic contrast-enhanced MR imaging-perfusion differences in malignant and benign lesions. Radiology, 232: 544-553, 2004.

Kuhl, C. K. and Schild, H. H. Dynamic image interpretation of MRI of the breast. J Magn Reson Imaging, 12: 965-974, 2000.

Futterer, J. J., Heijmink, S. W., Scheenen, T. W., Veltman, J., Huisman, H. J., Vos, P., Hulsbergen-Van de Kaa, C. A., Witjes, J. A., Krabbe, P. F., Heerschap, A., and Barentsz, J. O. Prostate cancer localization with dynamic contrast-enhanced MR imaging and proton MR spectroscopic imaging. Radiology, 241: 449-458, 2006.

Padhani, A. R., Gapinski, C. J., Macvicar, D. A., Parker, G. J., Suckling, J., Revell, P. B., Leach, M. O., Dearnaley, D. P., and Husband, J. E. Dynamic contrast enhanced MRI of prostate cancer: correlation with morphology and tumour stage, histological grade and PSA. Clin Radiol, 55: 99-109, 2000.

Kuhl, C. K., Schild, H. H., and Morakkabati, N. Dynamic bilateral contrast- enhanced MR imaging of the breast: trade-off between spatial and temporal resolution. Radiology, 236: 789-800, 2005.

Furman-Haran, E., Grobgeld D.,, Kelcz, F., and Degani, H. The critical role of spatial resolution in dynamic contrast enhanced breast MRI. J Magn. Res. Imaging, 13: 862-867, 2001.

Degani, H., Gusis, V., Weinstein, D., Fields, S., and Strano, S. Mapping pathophysiological features of breast tumors by MRI at high spatial resolution. Nat Med, 3: 780-782, 1997.

Kelcz, F., Furman-Haran, E., Grobgeld, D., and Degani, H. Clinical testing of high-spatial-resolution parametric contrast-enhanced MR imaging of the breast. AJR Am J Roentgenol, 179: 1485-1492, 2002.

Evelhoch, J., Garwood, M., Vigneron, D., Knopp, M., Sullivan, D., Menkens, A., Clarke, L., and Liu, G. Expanding the use of magnetic resonance in the assessment of tumor response to therapy: workshop report. Cancer Res, 65: 7041-7044, 2005.

Evelhoch, J. L. Key factors in the acquisition of contrast kinetic data for oncology. J Magn Reson Imaging, 10: 254-259, 1999.

Jeswani, T. and Padhani, A. R. Imaging tumour angiogenesis. Cancer Imaging, 5: 131-138, 2005.

Leach, M. O., Brindle, K. M., Evelhoch, J. L., Griffiths, J. R., Horsman, M. R., Jackson, A., Jayson, G. C, Judson, I. R., Knopp, M. V., Maxwell, R. J., McIntyre, D., Padhani, A. R., Price, P., Rathbone, R., Rustin, G. J., Tofts, P. S., Tozer, G. M., Vennart, W., Waterton, J. C, Williams, S. R., and Workman, P. The assessment of antiangiogenic and antivascular therapies in early-stage clinical trials using magnetic resonance imaging: issues and recommendations. Br J Cancer, 92: 1599-1610, 2005.

Padhani, A. R. MRI for assessing antivascular cancer treatments. Br J Radiol, 76 Spec No. 1: S60-80, 2003.

Jemal, A., Murray, T., Ward, E., Samuels, A., Tiwari, R. C, Ghafoor, A., Feuer, E. J., and Thun, M. J. Cancer statistics, 2005. CA Cancer J Clin, 55: 10-30, 2005.

Tofts, P. S. Modeling tracer kinetics in dynamic Gd-DTPA MR imaging. J Magn Reson Imaging, 7/ 91-101 , 1997.

Tofts, P. S., Brix, G., Buckley, D. L., Evelhoch, J. L., Henderson, E., Knopp, M. V., Larsson, H. B., Lee, T. Y., Mayr, N. A., Parker, G. A., Port, R. E., Taylor, J., and Weisskoff, R. M. Estimating kinetic parameters from dynamic contrast-enhanced T(1)-weighted MRI of a diffusable tracer: standardized quantities and symbols. J Magn Reson Imaging, 10: 223-232, 1999.

Galbraith, S. M., Lodge, M. A., Taylor, N. J., Rustin, G. J., Bentzen, S., Stirling, J. J., and Padhani, A. R. Reproducibility of dynamic contrast-enhanced MRI in human muscle and tumours: comparison of quantitative and semi-quantitative analysis. NMR Biomed, 15: 132-142, 2002.

Jesberger, J. A., Rafie, N., Duerk, J. L., Sunshine, J. L., Mendez, M., Remick, S. C, and Lewin, J. S. Model-free parameters from dynamic contrast-enhanced-MRI: sensitivity to EES volume fraction and bolus timing. J Magn Reson Imaging, 24: 586-594, 2006.

Yoo, S. S., Gil Choi, B., Han, J. Y., and Hee Kim, H. Independent component analysis for the examination of dynamic contrast-enhanced breast magnetic resonance imaging data: preliminary study. Invest Radiol, 37: 647-654, 2002.

Twellmann, T., Saalbach, A., Gerstung, O., Leach, M. O., and Nattkemper, T. W. Image fusion for dynamic contrast enhanced magnetic resonance imaging. Biomed Eng Online, 3: 35, 2004.

Walker-Samuel, S., Leach, M. O., and Collins, D. J. Evaluation of response to treatment using DCE-MRI: the relationship between initial area under the gadolinium curve (IAUGC) and quantitative pharmacokinetic analysis. Phys Med Biol, 51: 3593-3602, 2006.

Cootes, T., Hill, A., Taylor, C, and Haslam, J. The use of active shape models for locating structures in medical images. Image and Vision Computing, 12: 355-365, 1994.

Razifar, P., Axelsson, J., Schneider, H., Langstrom, B., Bengtsson, E., and Bergstrom, M. A new application of pre-normalized principal component analysis for improvement of image quality and clinical diagnosis in human brain PET studies—clinical brain studies using [11C]-GR205171 , [11 C]-L-deutehum-deprenyl, [11 C]-5-Hydroxy-L-Tryptophan, [11 C]-L-DOPA and Pittsburgh Compound-B. Neuroimage, 33: 588-598, 2006.

Furman-Haran, E. and Degani, H. Parametric analysis of breast MRI. J Comput Assist Tomogr, 26: 376-386, 2002.

Twellmann, T., Lichte, O., and Nattkemper, T. W. An adaptive tissue characterization network for model-free visualization of dynamic contrast-enhanced magnetic resonance image data. IEEE Trans Med Imaging, 24: 1256-1266, 2005.

Hassid, Y., Furman-Haran, E., Margalit, R., Eilam, R., and Degani, H. Noninvasive magnetic resonance imaging of transport and interstitial fluid pressure in ectopic human lung tumors. Cancer Res, 66: 4159-4166, 2006.

Furman-Haran, E., Grobgeld, D., Kelcz, F., and Degani, H. Critical role of spatial resolution in dynamic contrast-enhanced breast MRI. J Magn Reson Imaging, 13: 862-867, 2001.

Shapiro, S., Coleman, E. A., Broeders, M., Codd, M., de Koning, H., Fracheboud, J., Moss, S., Paci, E., Stachenko, S., and Ballard-Barbash, R. "Breast cancer screening programmes in 22 countries: current policies, administration and guidelines, International Breast Cancer Screening Network (IBSN) and the European Network of Pilot Projects for Breast Cancer Screening" Int J Epidemiol 27, 735-742 (1998).

Green, B. B. and Taplin, S. H. "Breast cancer screening controversies" J Am Board Fam Pract 16, 233-241 (2003).

Blanks, R. G., Moss, S. M., McGahan, C. E., Quinn, M. J., and Babb, P. J. "Effect of NHS breast screening programme on mortality from breast cancer in England and Wales, 1990-8: comparison of observed with predicted mortality" Bmj 321, 665-669 (2000).

Jatoi, I. and Miller, A. B. "Why is breast-cancer mortality declining?" Lancet Oncol 4, 251-254 (2003).

Degani, H., Gusis, V., Weinstein, D., Fields, S., and Strano, S. "Mapping pathophysiological features of breast tumors by MRI at high spatial resolution" Nature Med 3, 780-782 (1997).

Eyal, E. and Degani, H. "Model-based and model-free parametric analysis of breast dynamic-contrast-enhanced MRI" NMR Biomed, Jan;22(1):40-53. (2007).

Lee, S. H., Kim, J. H., Kim, K. G., Park, J. S., Park, S. J., and Moon, W. K. "Optimal Clustering of Kinetic Patterns on Malignant Breast Lesions: Comparison between K-means Clustering and Three-time-points Method in Dynamic Contrast-enhanced MRI" Conf Proc IEEE Eng Med Biol Soc 1, 2089-2093 (2007).

Padhani, A. R., Harvey, C. J., and Cosgrove, D. O. Angiogenesis imaging in the management of prostate cancer. Nat Clin Pract Urol, 2: 596-607, 2005.

* cited by examiner

Fig. 2A
1st eigen state
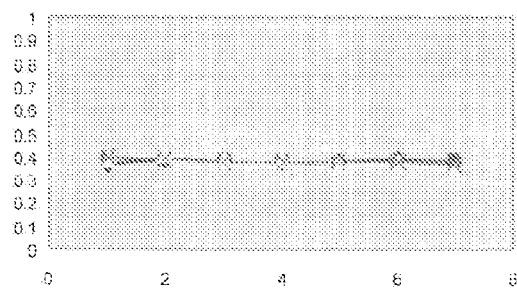
Fig. 2B
2nd eigen state
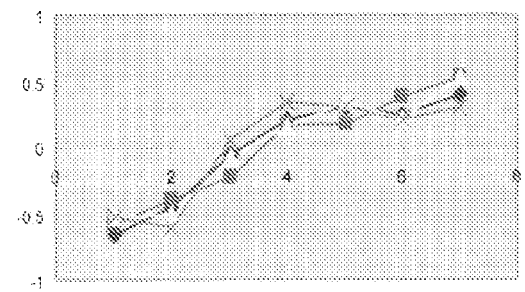
3rd eigen state: cancer cases
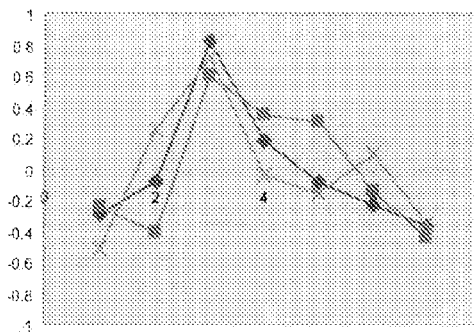
3rd eigen state: benign cases
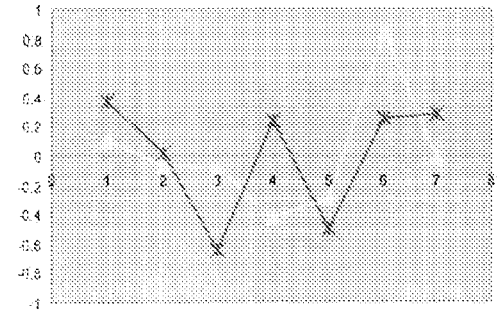
Fig. 2C
Fig. 2D Fig. 8A(1)  
3TP analysis
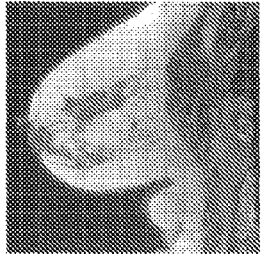
Fig. 8A(2)  
2nd rotated eigen vector
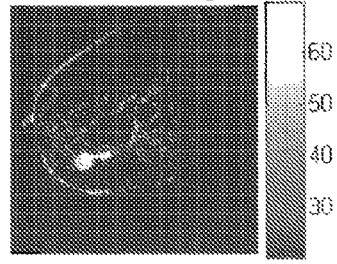
Fig. 8A(3)  
3rd rotated eigen vector
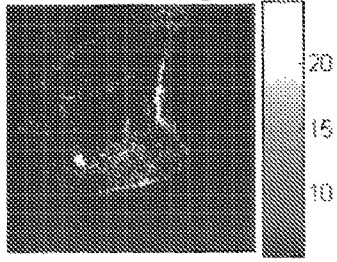
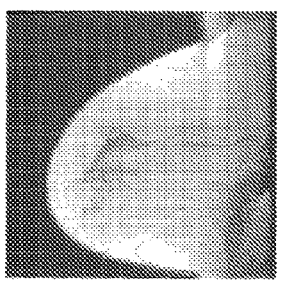
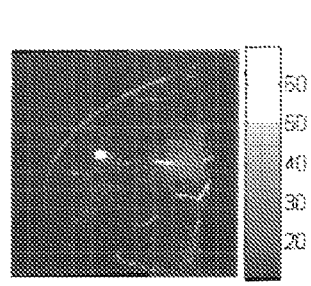
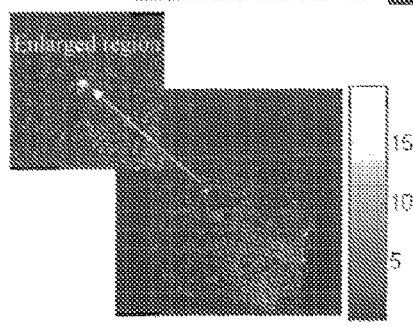
Fig. 8B(1)
Fig. 8B(2)
Fig. 8B(3)
Fig. 9A(1)
Fig. 9A(2)
Fig. 9A(3)
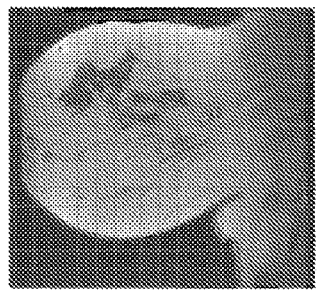
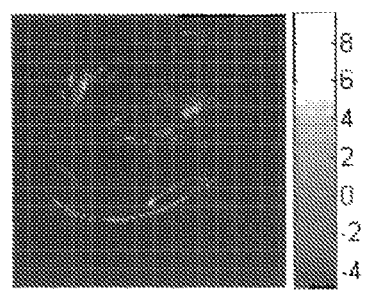
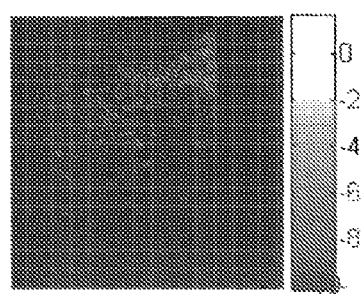
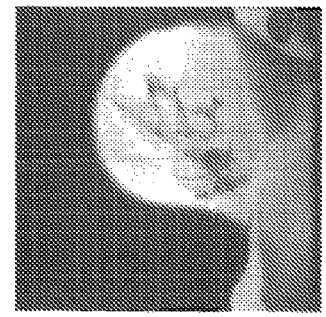
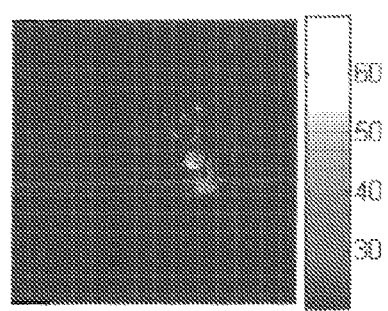
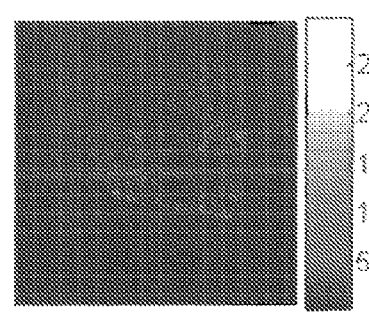
Fig. 9B(1)
Fig. 9B(2)
Fig. 9B(3)

METHOD AND APPARATUS FOR COMPUTER-AIDED DIAGNOSIS OF CANCER AND PRODUCT

BACKGROUND OF THE INVENTION

1. Field of Invention

The present invention relates to a method and apparatus and product for computer-aided diagnosis of cancer, and more particularly, to the diagnosis of breast cancer.

2. Prior Art

The use of diffusible tracers to probe the physiology of tissue has had a long history [see, for example, (1-3)]. With the advent of MRI (Magnetic Resonance Imaging) and the use of low molecular weight lanthanide (such as gadolinium) based contrast agents there has been a great deal of interest in developing novel approaches for the acquisition and analysis of dynamic contrast enhanced MRI (DCE-MRI) data. DCE-MRI involves the acquisition of serial MR images prior to, during, and after the intravenous administration of a contrast agent (4, 5). The acquisition sequences are chosen to be sensitive to the effects of the contrast agent on the nuclear relaxation rates of the water protons in the tissue. Thus, the temporal changes in the signal intensity seen in the dynamic magnetic resonance images constitute a reflection of the uptake of the contrast agent from the blood vessels into the tumor tissue and its washout from the tissue back to the blood vessels. DCE-MRI has gained wide use in diagnostic practice because these uptake and washout processes, as well as the ability of the accumulated contrast agent to reveal or highlight the tumor morphological features, can aid in their characterization [for examples, see (6-12)]. For these reasons, DCE-MRI has become a standard of care for imaging human breast cancer (6-8, 13) and has also come to be used for imaging tumors in other organs; e.g., prostate (10-12, 14), and lung (9). From the diagnostic point of view, there are cumulative evidences that high spatial resolution is crucial (13, 15-17). Moreover, as DCE-MRI is based on the belief that by its very nature it should be sensitive to parameters such as tumor vascularity, vascular permeability, and the cellular density of the tumor (5, 20), it has been proposed as a surrogate imaging biomarker for use in assessing response to therapy, including anti-angiogenic therapy (5, 12, 13, 15-22).

In spite of the widespread use of DCE-MRI, and its usefulness for the aforementioned purposes, there are still ongoing debates about the protocols used to acquire such images, their subsequent analysis, and the accurate presentation of information derived from these studies. In general, the analysis of DCE-MRI data falls into one of three main categories: fitting the data to a pharmacokinetic model [usually a two-compartment model with an idealized arterial input function (23-27)]; semi-quantitative approaches [see, for example, (28, 29)]; and model free approaches such as independent component analysis (ICA)[e.g., (30)] or principal component analysis (PCA) [e.g., (31)].

Methods and apparatus for dynamic contrast-enhanced magnetic resonance imaging of the breast are known. Previous studies have shown that breast malignancies are associated with a pattern of rapid signal enhancement and early washout of the contrast agent that differs from the slower and persistent enhancement pattern seen in normal tissue and in benign breast tumors, suggesting increased angiogenic activity in carcinomas (10, 11).

To date, the analysis of DCE-MRI images of the breast, and other organs has been based in most clinical settings on two approaches: estimation of empirical parameters and parametric analysis based on fitting the data to a pharmacokinetic model, or on identifying patterns based on simulating a pharmacokinetic model and designing a model based protocol such as the Three Time Point method protocol by Degani et al (16,17). On one hand the empiric approaches offer simplicity, however, the resulting parameters may be highly dependent on the specific MRI acquisition protocol employed. Therefore, it may be difficult to accurately correlate the parameters with underlying tumor physiology, and to compare the values of these parameters across different imaging sites. On the other hand, although the pharmacokinetic modeling can yield standardized, physiologically relevant parameters fitting of the dynamic curves on a pixel-by-pixel basis may suffer from the fact that the images are rather noisy; therefore, the fitting algorithms may yield either imprecise or inaccurate estimates of these parameters. In addition, in most cases, an idealized arterial input function is assumed; however, this assumption may not be correct. Alternatively, one may choose to determine an arterial input function In clinical practice, however, this may not be routinely feasible. Furthermore, the two-compartment model does not take into account a number of other factors which could affect the accuracy of the analysis, including the presence of pressure gradients and interstitial diffusion, both of which may alter the dynamic uptake and wash-out patterns. Nevertheless, these approaches have shown fairly good sensitivity and specificity for detecting breast lesions and differentiating benign from malignant breast tumors (7, 17).

Breast cancer is the most common malignancy among women and a major health burden worldwide. The mortality rate from breast cancer has been fairly constant in western countries, and since 1990 a decrease has been detected where screening has been introduced (63-65). One of the indirect beneficial effects of screening might have been a shift towards earlier diagnosis of breast cancer, as a result of the publicity surrounding the disease and its prevention (66). Currently, X-ray and ultrasound mammography are the leading methods used for screening the female population and detect breast cancer. However, breast magnetic resonance imaging (MRI), initiated in the 1980s (67) and particularly, contrast enhanced MRI using Gd-based contrast agents, and demonstrated capability to delineate breast lesions (68). Thus, contrast enhanced breast MRI emerged to become an important adjunct tool for detecting and diagnosing breast lesions, as well as monitoring response to breast cancer treatment (69, 70).

Overall, contrast enhanced MRI exhibits very high sensitivity but variable specificity in discriminating benign from malignant breast diseases, particularly due to the lack of standardization. Currently, a wide range of sequences and protocols, image processing methods, and interpretation criteria are being used. The heterogeneity of breast lesions, particularly of the malignant ones, requires imaging at high spatial resolution (71, 72), yet, obtaining accurate kinetic data requires high temporal resolution (73). Currently, however, it is not possible to achieve simultaneously both high spatial and temporal resolution with a practical signal to noise ratio. Most clinical analyses are based on empirical observations and criteria which depend on readers' experience (74-76). Nevertheless, attempts have been made to better understand the origin of the contrast observed in breast lesions using physiological models that take into account the vascular and tissue-specific features that influence tracer perfusion (77). These model based studies usually yield parametric images that quantitatively map the properties of the microvascular network.

SUMMARY OF THE INVENTION

The object of the present invention concerns a method and apparatus and product for computer-aided diagnosis of cancer, and more particularly, to the diagnosis of breast cancer that utilizes a hybrid approach of model free and model derived methods. It is based on a learning process that employs principal component analysis (PCA) of DCE-MRI datasets of the breast, in order to overcome part of the drawbacks of the approaches described previously, followed by analysis with the Three Time Point Method that provides parametric maps obtained by using a mathematical model to calculate DCE images, and then, a fusion process between the PCA and the Three time Point method to yield diagnostic improvement. PCA is a multivariate image analysis tool commonly used to analyze dynamic images in nuclear medicine and in MRI (31, 53-55). PCA has been applied to expose the patterns of dynamic contrast enhanced MRI data of the breast (31). PCA is usually applied for geometric shape representation, as a data normalization method, for dimension reduction, and for filtering noise prior to subsequent model-based data analysis.

In the present invention the model-free PCA method is successfully applied in tandem with a model-based kinetic approach, to the selection of physiologically relevant patterns of enhancement that discriminate between normal and malignant tissues of the breast and between benign and malignant breast lesions, as well as, filtering out instrumental and random noise. Moreover, by use of the invention, this integrated processing method is rapid, standardized and demonstrates a high degree of sensitivity and specificity for detecting and diagnosing breast cancer.

Accordingly, the object of the present invention is a method and apparatus and product for computer-aided diagnosis of cancer, and more particularly, to the diagnosis of breast cancer that involves the development and integration of a mathematical, model-free analysis and a kinetic, model based analysis of dynamic contrast-enhanced magnetic resonance imaging (DCE-MRI) of tissues that develop malignancies, such as, applied to the breast The present invention presents a general hybrid method for analyzing dynamic contrast enhanced images integrating a mathematical, model-free technique with a model derived method that characterizes tissue microvasculature function. The application of this new hybrid method is for breast cancer diagnosis and for other cancers such as lung, prostate, ovarian, pancreatic etc. The model free method employs principal component analysis and yielded eigenvectors of which two were relevant for characterizing breast malignancy. The physiological features and diagnostic relevance of the two eigenvectors were obtained by performing a quantitative correlation with the model based Three Time Point method which led to the selection of an optimized rotation angle for rotating the two relevant eigenvectors to new rotated eigenvectors. These new rotated eigenvectors have a physiological meaning and their projection coefficient maps provide improved diagnostic capacity for differentiating benign from malignant breast lesions. Projection maps of the rotated eigenvectors resulting from the hybrid method that specifically related the wash-out rate of the contrast agent depicted with high accuracy breast cancer. Overall, this hybrid method is fast, standardized, and yields parametric images characterizing tissue microvascular function. It can improve breast cancer detection and be potentially extended as a computer-aided tool for the detection and diagnosis of other cancers.

BRIEF DESCRIPTION OF THE DRAWINGS

FIG. 2 shows graphical representation of the results for PCA analysis of the most important 3 eigenvectors (also termed eigen-states) derived from a representative breast slice in 5 patients. The plots show the first two most significant eigenvectors (a,b) for all cases, benign and malignant. The vectors of the $3^{rd}$ eigen-state are presented separately for cancers (c) and benign (tissue) (d) showing a different pattern (The scales are in arbitrary units).

FIG. 8 shows a 3TP colored image overlaid on a regular breast image of a slice with breast cancer that depicts the presence of cancer in two patients (a1;b1) and their corresponding rotated $2^{nd}$ and $3^{rd}$ eigenvectors (a2,a3; b2,b3). The regions with high intensity in both projection maps indicate the presence of cancer.

FIG. 9 shows a 3TP colored image overlaid on a regular breast image of a slice with breast benign disease that depicts the presence of a benign lesion in two patients (a1;b1) and their corresponding rotated $2^{nd}$ and $3^{rd}$ eigenvectors (a2,a3; b2,b3). Benign tumors show high intensity only in the projection coefficient maps of the $2^{nd}$ rotated eigenvector but null or negative intensity in the projection coefficient maps of the third rotated eigenvector.

A1-A7: T1 weighted precontrast (A1&A2) and post contrast (A3-A7) images. The white arrow points the location of the enhanced lesion. The star marks an area with non-uniform intensity due to field/frequency inhomogeneity.

B1-B7: The seven eigenvectors derived from PCA decomposition of the T1-weigted intensity scaled images using the entire breast ROI, sorted from the largest to the smallest.

C1-C7: Projection coefficient maps of the corresponding eigenvectors, the color bar range is [200,420] [10,100] [3,30] [3,30] [−10,10] [−10,10] [−10,10], respectively.

D: A plot of the eigen-values corresponding to the eigenvectors (logarithmic scale).

Figure 18:
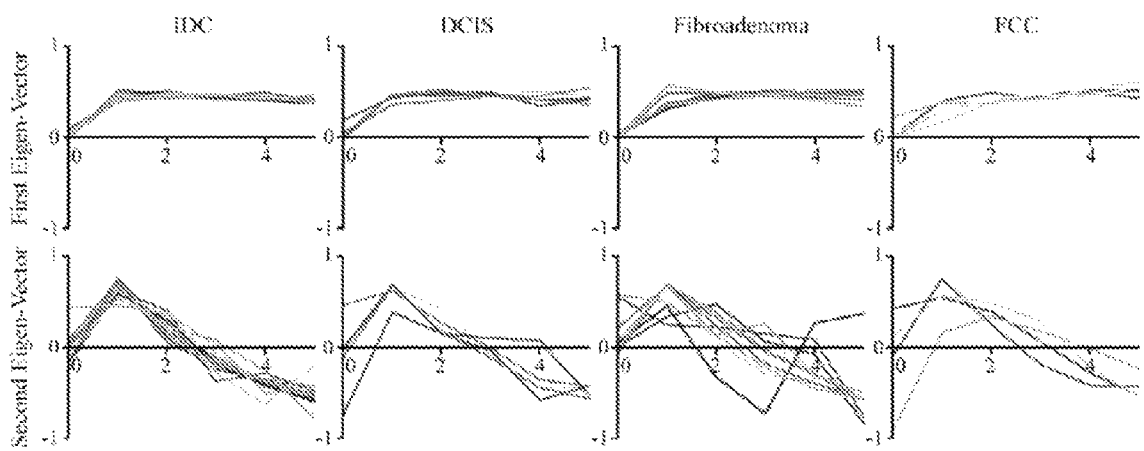

FIG. 18 shows PCA of enhancement images, using lesion ROI in a central slice of the lesion, showing the plots of the first and second most significant eigenvectors for all cases, grouped by the lesion type (The scales are in arbitrary units).

Figure 19:
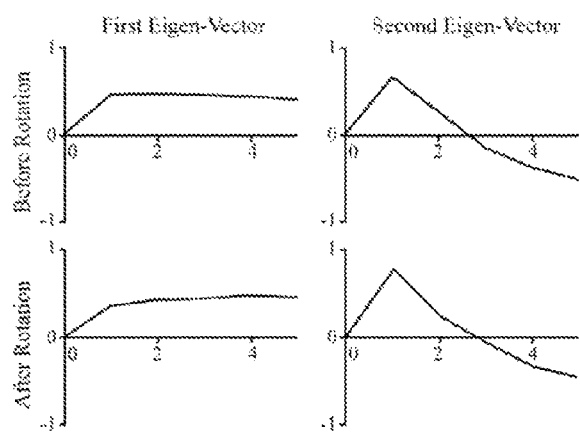

FIG. 19 shows the median pattern of the first and second eigenvectors, derived from PCA performed on enhancement images for a central slice of each malignant tumor (n=12) and using the tumor ROI, before (upper row) and after (lower row) axis clockwise rotation by 10 degrees.

Figure 20:
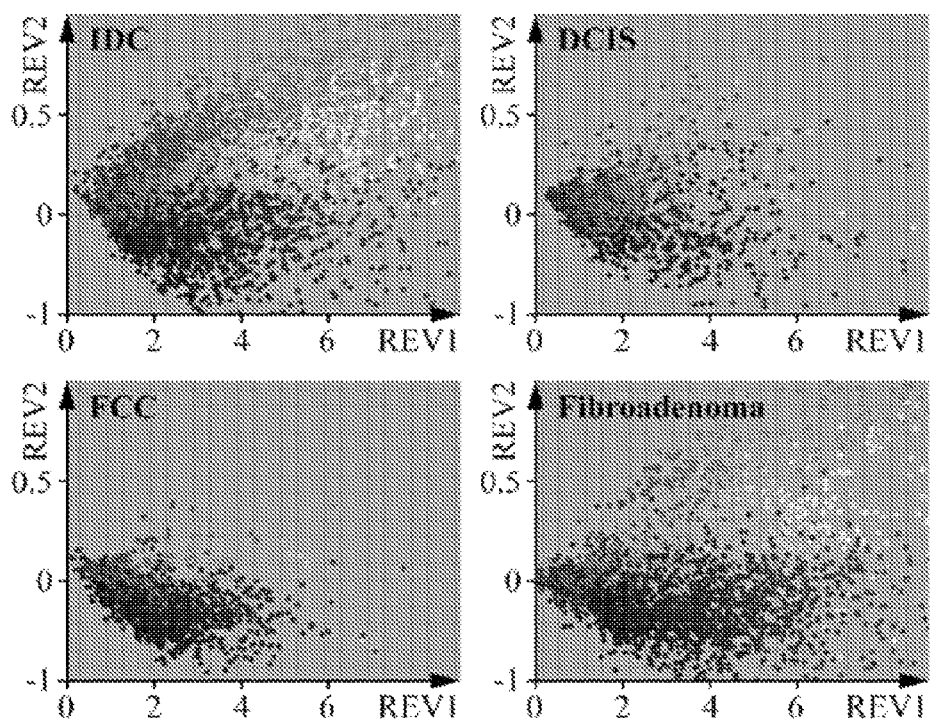

FIG. 20 shows the correlation between the first and second rotated eigenvector coefficients (REV1 and REV2, respectively) obtained from the PCA and the 3TP color-coded labeling. For each lesion type, the data were obtained from the central slice of all the lesions. Each point is a voxel with its location is determined by the values of the first and second eigenvector coefficients and its color labeling according to the 3TP method.

Figure 21:
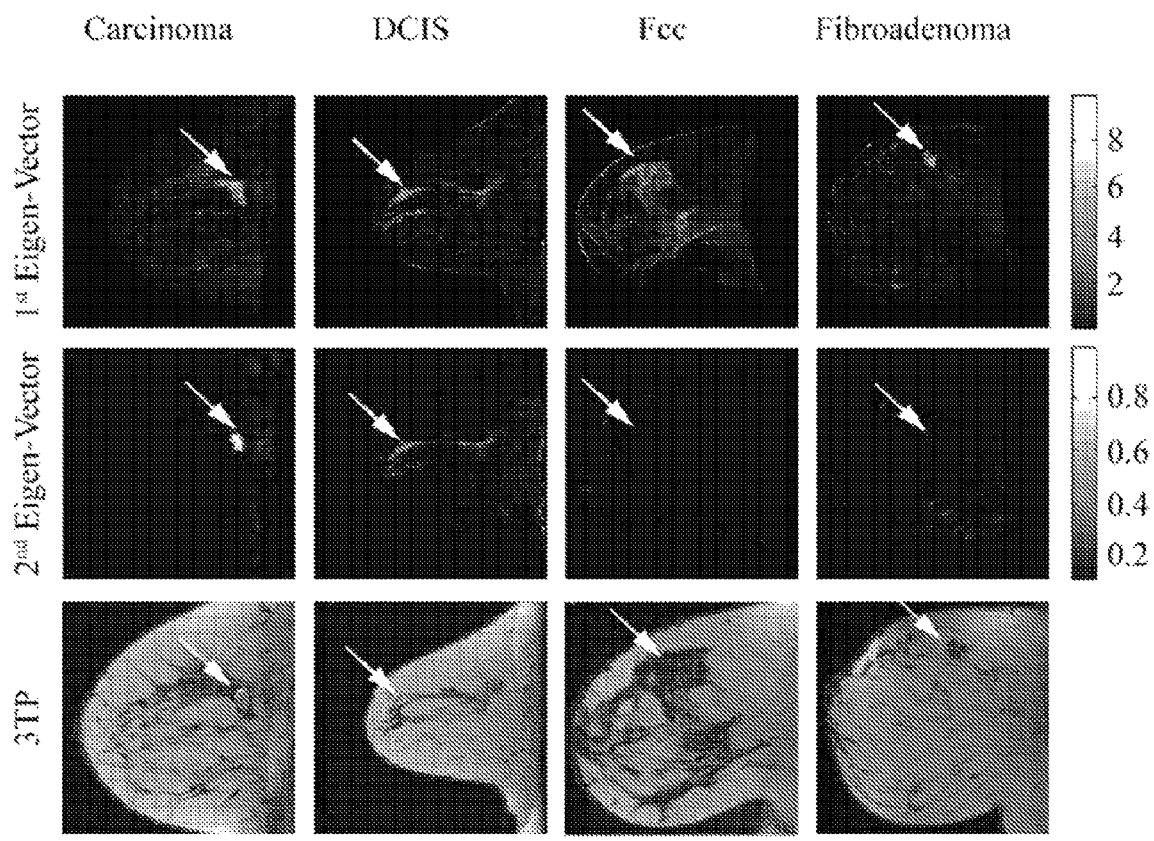

FIG. 21 shows parametric maps of the projection coefficients of the first rotated eigenvector (upper row), the second rotated eigenvector (middle row) and the 3TP analysis (lower row) for the various lesion types The rotated eigenvector maps were derived by projecting the data on the generalize rotated eigenvector-base. The white arrow points to the primary lesion.

Figure 22:
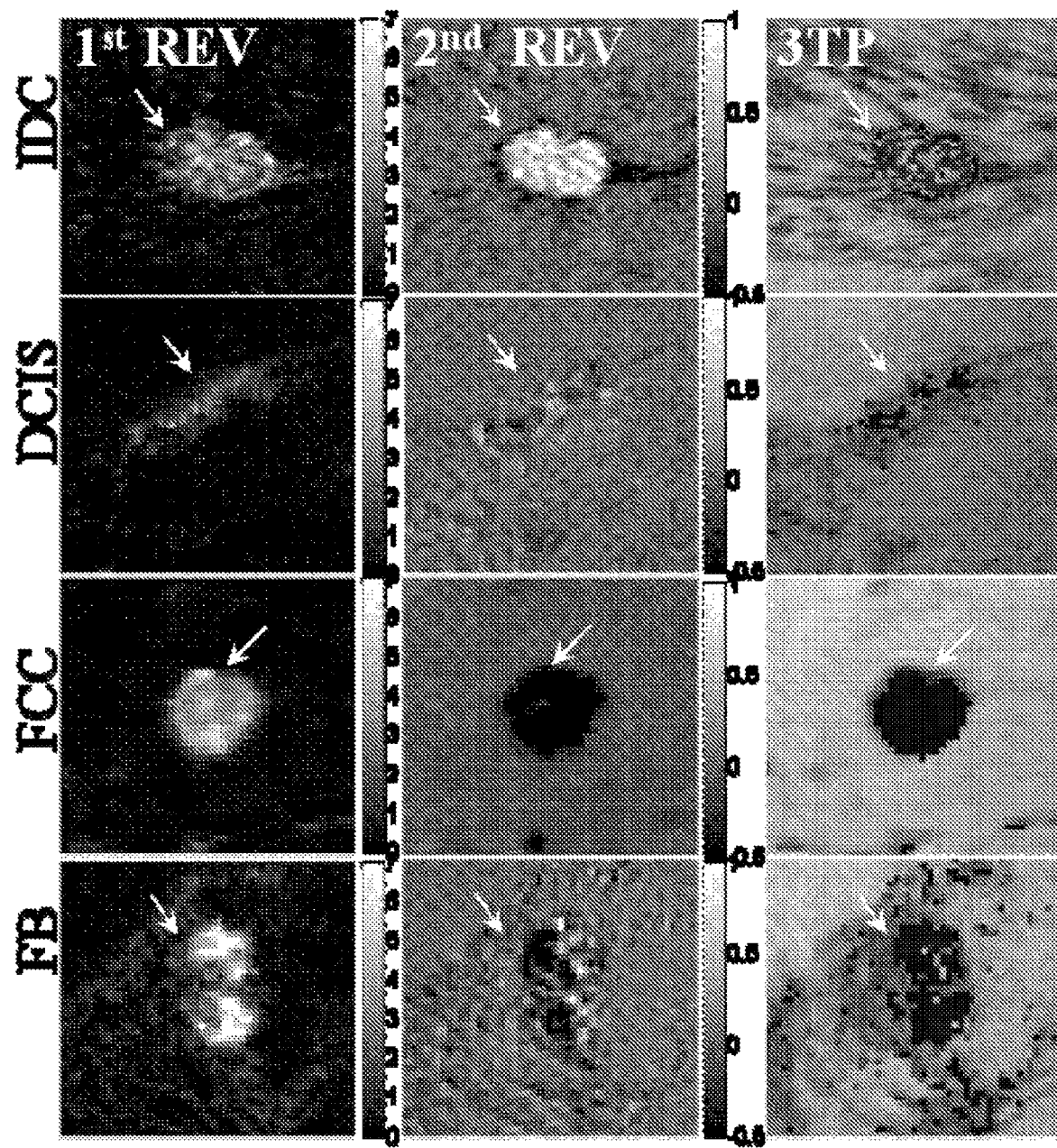

FIG. 22 shows the diagnostic evaluation and validation for enhancement images set. Shown are the projection coefficient maps of 1st and 2nd rotated eigenvectors (REVs) and the corresponding 3TP color coded maps.

Figure 23:
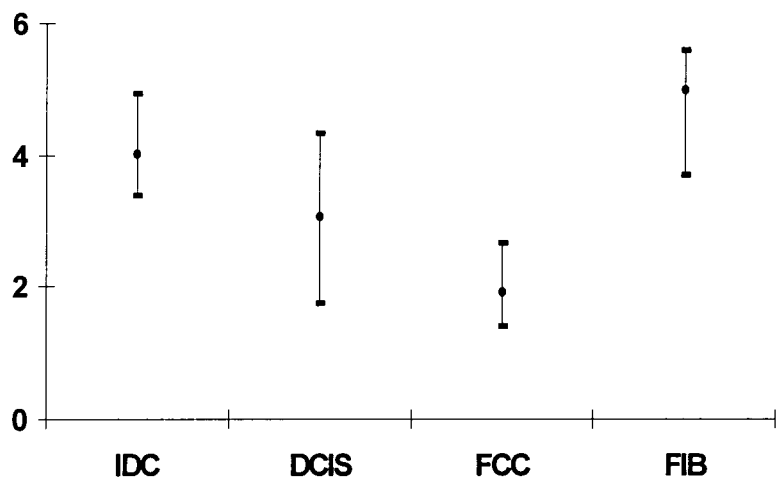

FIG. 23 shows median and IQR of 75 th percentile values within each of the groups of FIG. 22 for the first REV.

Figure 24:
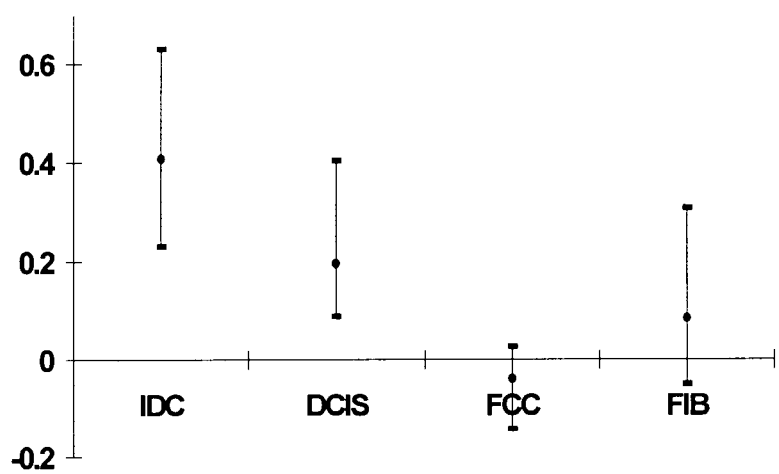

FIG. 24 shows median and IQR of 75 th percentile values within each of the groups of FIG. 22 for the second REV.

Figure 25:
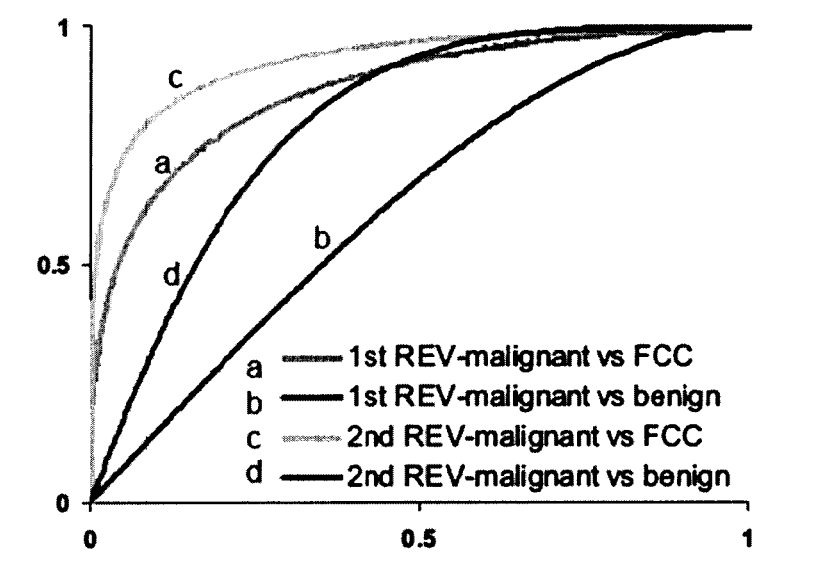

FIG. 25 shows receiver operating characteristic (ROC) curve analysis of the data of FIG. 22.

DETAILED DESCRIPTION OF PREFERRED EMBODIMENTS OF THE INVENTION

The goal of this invention is a method and apparatus that operates as a hybrid method with a developed and integrated mathematical, model-free analysis and a kinetic model based analysis of dynamic contrast-enhanced magnetic resonance imaging (DCE-MRI) of tissue, particularly breast, although the invention can be used with other tissue, such as lung, prostate, brain, ovary etc.

In one application of the invention, MRI of the breast has been performed in 5 patients 3 with breast cancer and 2 with benign breast disease using 1.5 Tesla scanner equipped with a dedicated breast coil. Seven sets of 3 dimensional dynamic contrast enhanced images were recorded at high spatial resolution, using gadopentetate dimeglumine as a contrast agent. Each such set underwent principal component analysis (PCA) and analysis by the three time point (3TP) software (see disclosure material of U.S. Pat. Nos. 6,353,803, 6,553,327, 6,611,778 and 7,110,903 all of which is here incorporated by reference in its entirety). Principal component analysis (PCA) of each dynamic set yielded a covariance matrix (7×7) and its corresponding eigenvalues and eigenvectors. This analysis, which could be readily reproduced for all cases examined, provided a common eigenvector basis for the PCA decomposition of any new case. The projection coefficient maps of the most dominant $1^{st}$ eigenvector showed high coefficients in the tissue defined as fat and appeared to reflect inhomogeneous field and differences in fat water resonance frequency. This eigenvector can be filtered out to improve image quality. The projection maps of the $2^{nd}$ and $3^{rd}$ eigenstates correlated with highly enhanced breast tissue and those of the $4^{th}$ to $7^{th}$ eigenvectors appeared to correlate to random noise. Correlation of the $2^{nd}$ and $3^{rd}$ eigenvectors and the 3TP labeling of color hue and intensity indicated that a rotation (of ~70 degrees) clockwise around the first eigenvector resulted in their congruence with the 3TP wash-in rate and wash-out patterns, respectively. Namely the rotated $2^{nd}$ eigen state correlated to the intensity changes of the colors in the 3TP labeling which indicate the rate of contrast agent wash-in to the tumor whereas the rotated $3^{rd}$ eigen state correlated with the color hue labeling of the 3TP which indicated the rate of contrast agent wash-out from the tumor to the blood. Furthermore, as most of the breast did not enhance, the black 3TP labeling (for non-enhancing voxels) exhibited close to null intensity in the projection maps of the $2^{nd}$ and $3^{rd}$ eigen states. Interestingly, the cancers showed high intensity in the projection maps of both the rotated $2^{nd}$ eigenvector and the rotated 3rd eigenvector depicting the localization of malignancy. In contrast, the benign lesions showed high intensity only in the rotated $2^{nd}$ eigenvector whereas null or negative intensity throughout the breast in the rotated 3rd eigenvector. Indeed the $3^{rd}$ eigenvector in benign breast lesions appears as a random noise component whereas in the cancers it has clear features of wash-out rate.

It is important to note that the congruence of the relevant PCA eigenvectors and the 3TP parameterization is tissue specific and can vary for tumors in different organs. The hybridization to get rotated eigenvectors requires the right application of the 3TP method in addition to the calculation of the eigenvectors. Quantitative analysis and algorithm were developed to achieve optimal congruence between the projection coefficients of the two eigenvectors and the 3TP labeling parameters in order to determine the optimal rotation angle.

The novel computer-aided method and apparatus based on integrating PCA and the 3TP algorithm for analyzing DCE-MRI datasets of breast gives good results. In a pilot study, it was demonstrated that the apparatus and method are capable of diagnosing breast tumors and differentiating between benign and malignant breast tumors with a high degree of accuracy.

Patients

The invention was tested for detection of cancer and included breast DCE-MRI of 5 patients, 3 with histologically confirmed breast cancer and two with histologically confirmed benign breast lesions.

MR Imaging

All patients for breast imaging underwent an MRI exam on a 1.5 T scanner (GE Medical Systems, Waukesha, Wis.) using an MRI devices breast coil (MRI devices, Waukesha, Wis.). The protocol of the DCE-MRI study was based on the 3TP method, with all instrumental parameters, time of injection, dose of contrast agent and temporal resolution described below judiciously selected using the calibration map of the 3TP method. A three dimensional gradient echo acquisition was employed using the following parameters: TR=15 msec, TE=4.2 msec, flip angle=30 degrees, FOV=16-18 cm, matrix=256×256, slice thickness 2.2-3.0 mm. Seven consecutive image sets were obtained over 14 min with contrast being injected three minutes after the beginning of the scan. Gadodiamide (Omniscan, Nycomed Laboratories. Princeton, N.J.) was injected, using a dose of 0.1 mmol/kg three minutes after the beginning of the scan series, i.e. one minute after the start of the second scan sequence. Contrast agent was administered at two ml/sec, followed by 15 ml of saline flush, also delivered at two ml/sec, using an automated pump (Spectris MR Injector, Medrad Corporation, Indianola, Pa.).

Image Processing

Registration: A basic translational registration tool was developed in-house, and utilized to correct planar motion in the different intensity scaled DCE images of the same dataset. Each image was aligned with the image which preceded it temporally, starting from the last time point, so that finally, all dynamic images were aligned to the first pre-contrast image.

Enhancement images: Parametric contrast-enhanced images were obtained using the standard definition of enhancement: $[I(t)-I(0)]/I(0)$, where $I(0)$ and $I(t)$ represent pre-contrast and post-contrast intensity values, respectively, for the same pixel.

Principal component analysis using intensity scaled images: Characterizing the patterns of contrast agent enhancement in the registered images comprised a learning step in which analysis of several dataset from different patients produced a common eigen-vector basis that served for the decomposition of principal components of each new case. This learning step included the following tasks:

(i) Organizing the dataset: the entire breast region of interest (ROI) was manually delineated for each aligned dataset d and central slice of the lesion, so that $|ROI_{d,s}|=N$. Each voxel v was associated with a state vector $u_v=(u_{1,v}, u_{2,v}, \ldots, u_{t,v})$, representing the signal intensity values measured at different time points t for that voxel. The data could then be represented by the following set: $\Gamma_{d,s}=\{u_i\}, 0 \leq i \leq N$.

(ii) Building the covariance matrix: The first-order covariance matrix of F was calculated, from which the following symmetric, positive matrix was derived:

$$COV_{d,s} = \frac{1}{N}\sum_{u \in \Gamma}(u-\bar{u})(u-\bar{u})^T \text{ and } \bar{u} = \frac{1}{N}\sum_{u \in \Gamma} u$$

(iii) Calculating the principal components: The linear PCA transformation was used to reduce the dimensionality of the data by mapping it to a new coordinate system of orthogonal axes. This method optimally minimizes the reconstruction error under the L2 norm. These axes represent the eigenvectors of $COV_{d,s}$ and are calculated by solving: $\lambda e = COV_{d,s} e$ and $E_{d,s}=\{e_i\}, 0 \leq i \leq t$.

The eigenvectors were indexed and sorted according to their eigenvalues; hence, $e_1$ represents the largest eigen-value and is referred as the first and dominant eigenvector.

(iv) Determining a common eigenvector-base: Calculation of the principal components produced a different eigen-base $E_{d,s}$ for every dataset d and slice s. The median eigen-base $E_{mid}$ was chosen as the representative, normalized eigen-base.

(v) Creating projection coefficient maps: Each pattern was then projected onto one of the eigenvectors, in order to associate each spatial position with a new scalar value of the weight of the principal component.

(vi) From the distribution of the coefficients in the projection maps of each eigenvector, it is possible to sort out the eigenvector reflecting instrumental/inhomogeneity RF field of the scanner or frequency chemical shift effects and filter out these artifacts obtaining a new set of intensity dynamic images free of such artifact according to the scheme in 14.

Alternatively, it is possible to use enhancement derived set of images obtained by normalizing the intensity of the post-contrast images to the intensity of the pre-contrast image, at pixel resolution. This enhancement data set is free of the scanner and frequency artifacts and yields t−1 eigen vectors (for t time point data-sets) which provide six projection maps of these eigenvectors.

Figure 15:
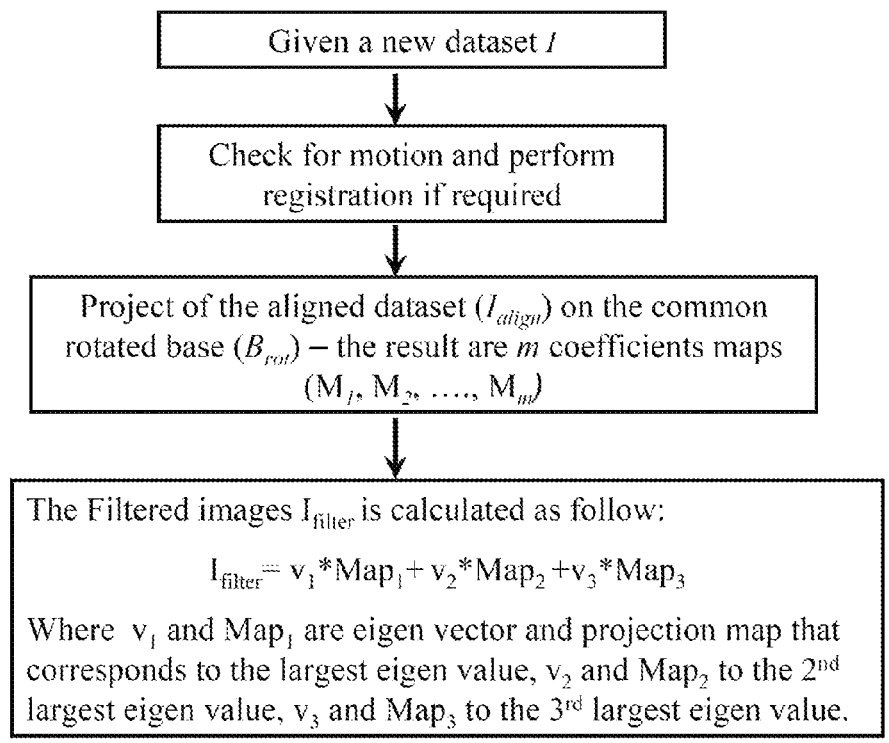
FIG. 15 shows a flow chart for random noise and its filtering using PCA projection.

(vii) From the distribution of the coefficients in the projection maps of each eigenvector it is possible to sort out the eigenvectors reflecting random noise and filter out the noise to obtain a corrected smooth dynamic data and intensity images according to the scheme in FIG. 15.

Correlation of PCA with the Three Time Point (3TP) Analysis:

A special algorithm (hereinafter called the "3TP" algorithm or method, now well known in the art and to persons of ordinary skill in the art) codes changes in signal intensity between three judiciously selected time points, one pre-contrast and two post-contrast (see disclosure material of U.S. Pat. Nos. 6,353,803, 6,553,327, 6,611,778 and 7,110,903 all of which is here incorporated by reference in its entirety). Color intensity (dark to bright) reflects rates of change in signal intensity in the time interval between the $1^{st}$ time point (pre-contrast) and the $2^{nd}$ time point (termed the "wash-in rate"). Color hue reflects changes in signal intensity between the $2^{nd}$ and $3^{rd}$ time points (termed the "wash-out pattern") according to the following scale: blue, for increased signal intensity; green, for no significant change; and red, for a decrease in signal intensity.

By means of the same color-coding scale, the 3TP method may also be used to calculate a model-based calibration map, for all possible values of the transcapillary transfer constants, which represent the physiological parameters affecting the distribution of the contrast agent in the tissue. This calibration map is used for selecting the three most optimal time points within a selected experimental protocol used for scanning a tissue, as well as, for relating color hue/color intensity coding of the 3TP labeling scheme to the transcapillary transfer constants and extracellular extravascular volume fraction (17). The 3TP type of calibration map calculated for the selected experimental conditions used in the testing of this invention showed that the optimal time points for image acquisition were for the breast: pre-contrast set (0 minutes); first post-contrast set (2 min post contrast) which is the third data set, and second post contrast set (6 min post contrast) which is the $5^{th}$ data set. These time points dictate a temporal resolution of the protocol and the injection time and may change depending on the experimental conditions and on the tissue and on the nature of the contrast agent.

Figure 10:
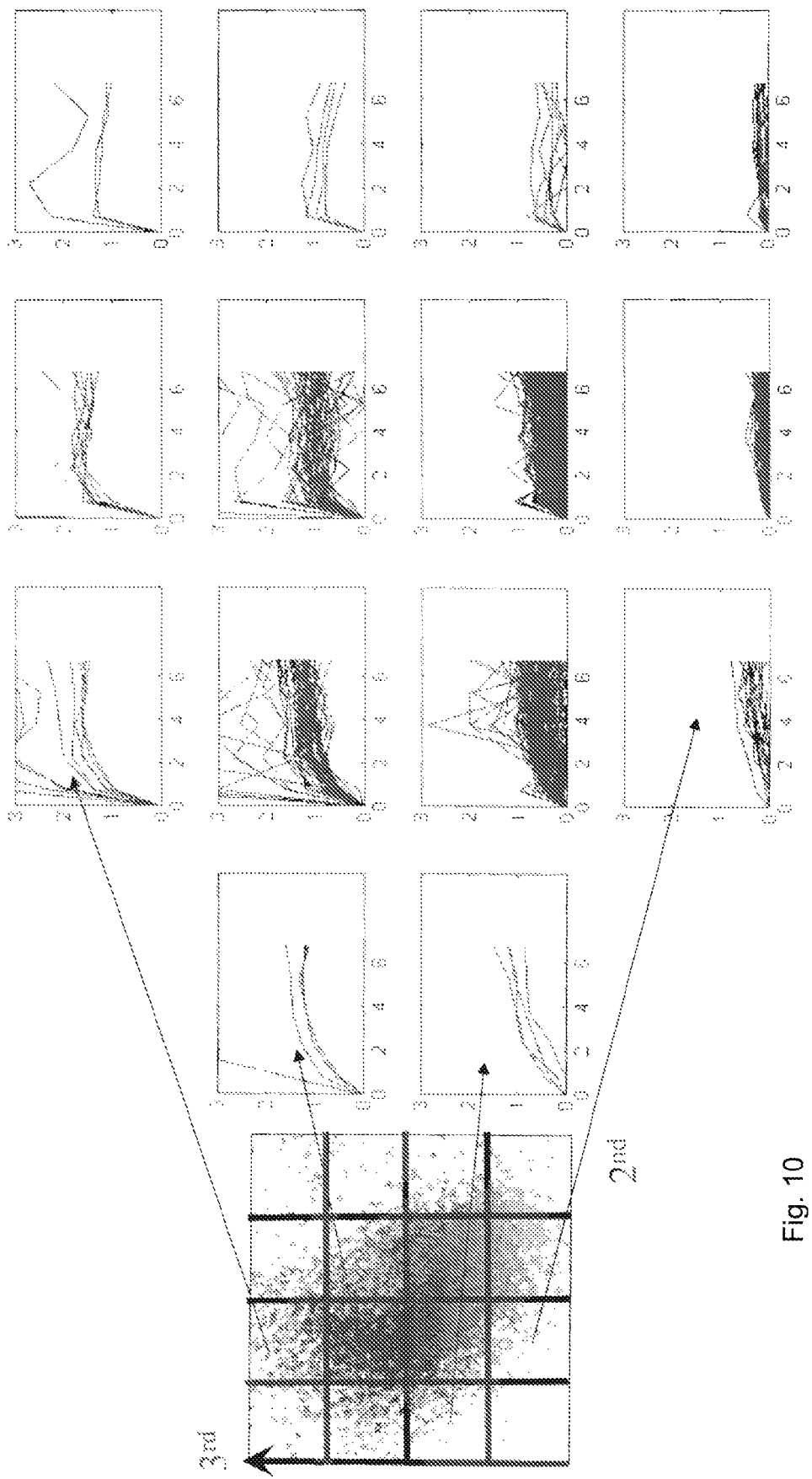
FIG. 10 shows the characteristic pattern at each grid location (sampling 3% of the patterns randomly for each area) derived from a typical breast slice. The resulting graphs show that the x axis corresponding to the projection coefficients of the $2^{nd}$ rotated eigenvector (also termed eigen states) spans the range of different enhancement patterns and the y axis corresponding to the projection coefficients of the 3rd rotated eigenvector is an enhancement scaling factor and matches the 3TP shades.

FIG. 10 shows pattern distribution of the $2^{nd}$ (x-axis) and $3^{rd}$ (y-axis) rotated eigenvectors. The sampling was 3% of the patterns in each grid location in the x-y plane.

Although the 3TP technique is not a standard method for the diagnosis of breast cancer, it can be used as a reference method instead of histology as was previously shown by Twellmann et al. for DCE-MRI of the breast (57). We confirmed the localization of tumors and their diagnosis by histopathological findings obtained from biopsies or after surgical removal. The correlation between the PCA components and the 3TP-derived parameters (color coded) were determined as follows:

(i) Correlation of the principal components with patterns derived from the 3TP method: The two dominant eigenvectors of diagnostic relevance, the $2^{nd}$ and $3^{rd}$ eigenvectors (when using intensity scaled images), or the $1^{st}$ and $2^{nd}$ eigenvectors when using enhancement (normalized to pre-contrast) images, were examined. The projection coefficients values of the two eigenvectors in the x and y axes, respectively, were correlated pixel by pixel with the 3TP technique represented by the 3TP coloring scheme.

The correlation between the $2^{nd}$ and $3^{rd}$ eigenvectors and the 3TP patterns indicated that after rotation of the x and y axes around the z-direction (the direction of the $1^{st}$ eigenvector), the $2^{nd}$ eigenvector comes to represent the 3TP wash-in pattern, and the $3^{rd}$ eigenvector comes to represent the wash-out rate, yielding a new base $E_{rot}$. Similarly, the correlation between the $1^{st}$ and $2^{nd}$ eigenvectors of the enhancement images and the 3TP patterns also indicated the need for a simultaneous rotation of the x an y axes around the z-axis in order to accurately represent the 3TP wash-in and wash out parameters.

The rotation program moves on all possible angles starting with an initial guess (or with zero angle if no guess was given) and finds the angle that satisfies best the conditions set by the program for an optimal angle. The conditions (criteria) for selecting an angle are defined in the program and can be:

1. All green and red 3TP labeled voxels are positive regarding the $3^{rd}$ eigenvector axis (representing after rotation washout) and all blue voxels have negative value for this eigenvector axis. Similarly for enhancement data set the conditions will refer to the $2^{nd}$ eigenvector axis.

2. All red voxels and half of the green voxels with the highest intensity are positive regarding the $3^{rd}$ eigenvector axis and all blue voxels and the remaining green voxels are negative on this axis 3. Apply 1 or 2 and add another condition for the $2^{nd}$ eigenvector axis using a linear correlation fitting between the intensity and this eigenvector coefficients and choosing the angle that yields the highest correlation coefficient ($R^2$) for the linear correlation.

(ii) Calculation of the rotated eigenvectors and their distribution: Given a new dataset $\Gamma$, the projection $P_{d,s}$, of the input data on $E_{rot}$ was calculated as follows:

$$P_{d,s} = \Gamma E_{rot}^{-1}$$

yielding projection coefficient maps of the new, rotated $2^{nd}$ and $3^{rd}$ eigenvectors for the intensity scaled images (or rotated $1^{st}$ and $2^{nd}$ eigenvectors for the enhancement images).

Note that following the learning step, the analysis of each new case using the rotated eigen-base is both time- and computer memory-efficient and that neither ROI delineation nor principal component calculations are required for each new case.

Figure 12:
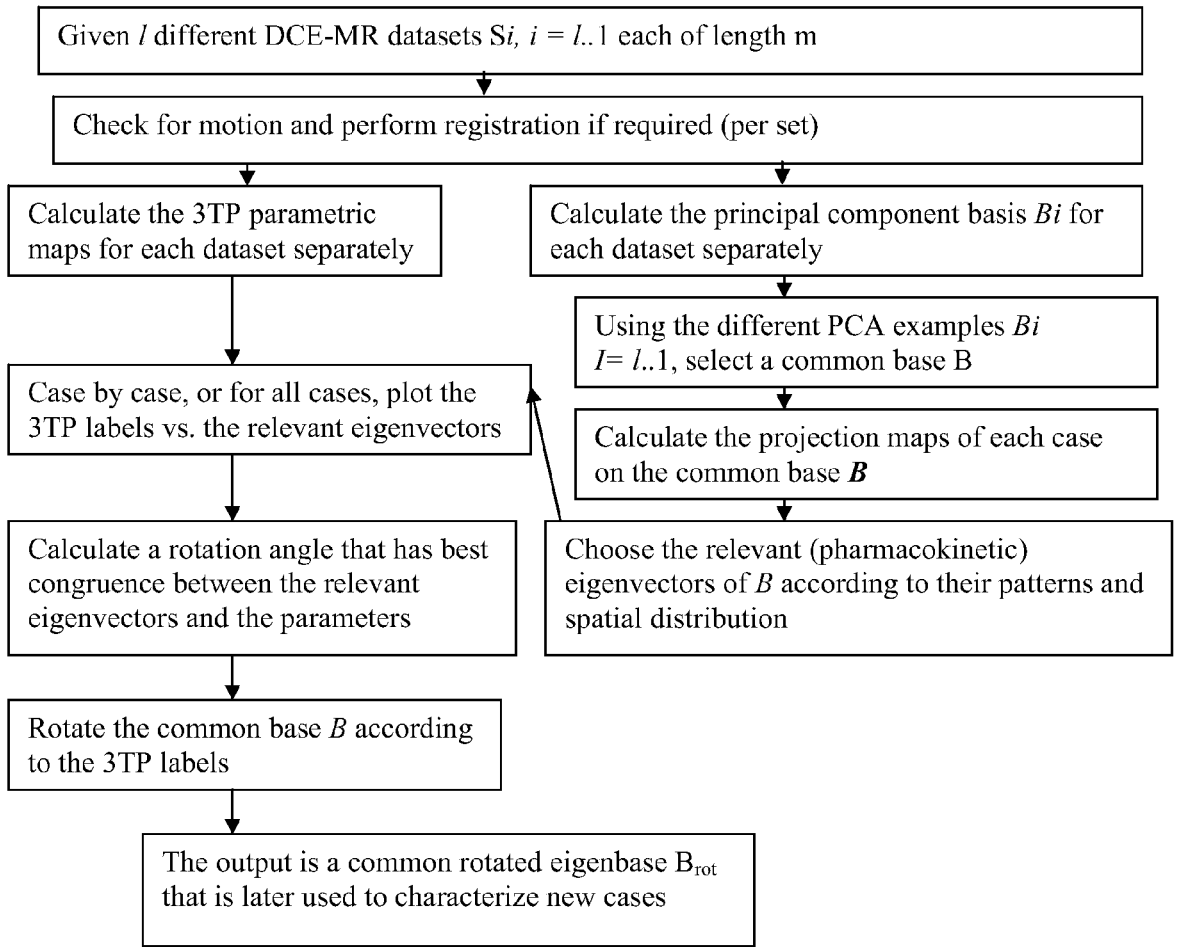
FIG. 12 shows a flow chart for the learning step of constructing a general eigenvector base and fusion with the 3TP method to obtain transformed (rotated) eigenvectors.

The overall learning process leading to the construction of a common base of eigenvectors and the fusion with the 3TP color coded parameters to yield a common transformed (for example rotated) eigenvectors of a physiological/diagnostic relevance is shown in FIG. 12.

Figure 13:
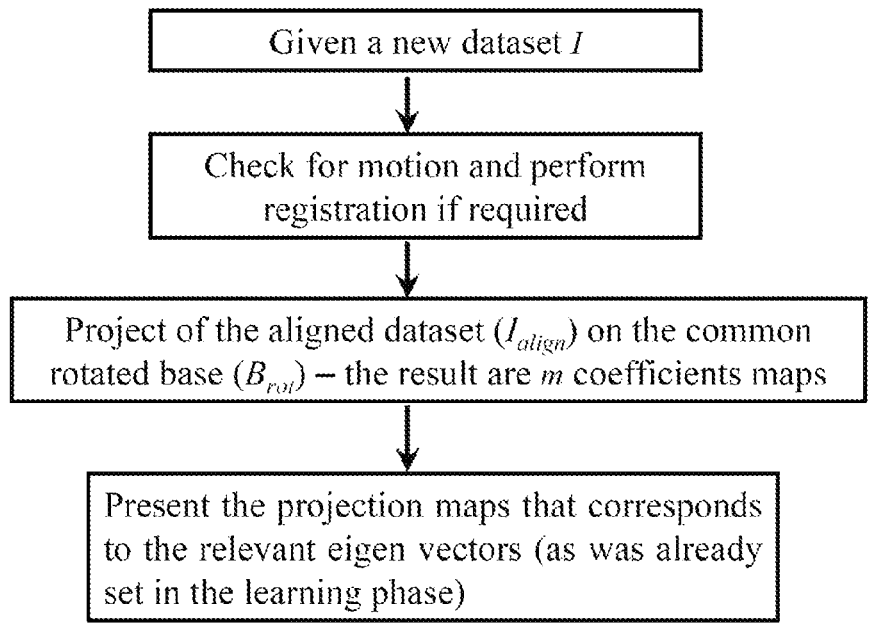
FIG. 13 shows a flow chart for analysis of a new case using the rotated eigenvector base.
Figure 14:
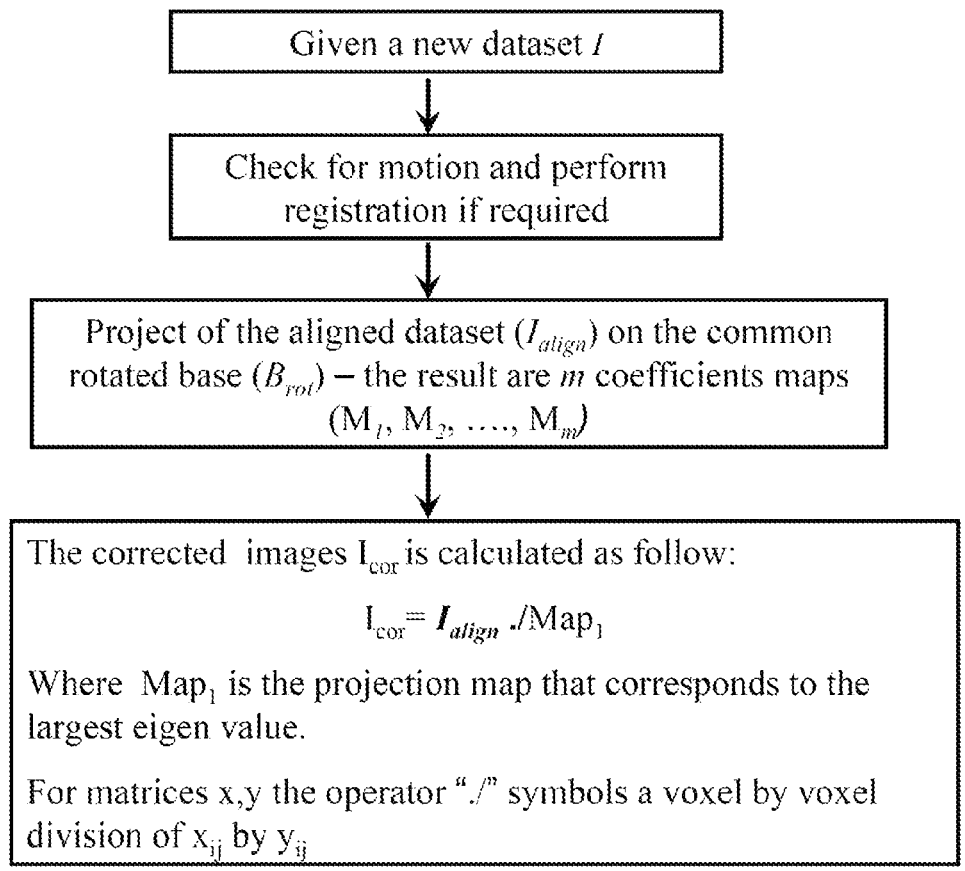
FIG. 14 shows a flow chart for correcting radiofrequency or other instrumental variations using PCA projection.

The scheme to analyze a new case using a common rotated eigenvector-base obtained as described in FIG. 12 is shown in FIG. 13.

Histological Examination

The diagnosis of the breast lesions was obtained by histopathology analysis of specimens obtained by excision biopsy, core biopsy, or fine-needle aspiration by experienced pathologists, Wisconsin Medical Center.

Statistical Analysis

The statistical relevance of the two rotated eigenvectors was evaluated using Kruskal-Wallis (KW) test for significance with multiple comparisons between the various groups of breast lesion (infiltrating ductal carcinoma—IDC; ductal carcinoma in situ—DCIS; fibrocystic changes—FCC; fibroadenoma—FB), as well as with receiver operating characteristic (ROC) curves. These curves provided a graphical plot of the sensitivity vs. 1-specificity. The median or 75th percentiles of the projection coefficients of either 1st or 2nd rotated eigenvectors (obtained from enhancement data set) served as predictors and histological labeling served as a classifier.

The type of lesion and its localization was based on histological confirmation as well as x-ray and ultrasound mammography findings. The area under the ROC curve (AUC) is indicative of the ability of the variable to correctly separate between benign and malignant breast tissue as well as between groups such as IDC+FDCIS and FCC lesions, or IDC and FB lesion.

Results

The decomposition of the principal components in the breast was performed per slice within each dataset, repeating the process for several central slices, for five breast cases.

A typical example of the first 7 (eigenvectors (also termed eigenstates) and the corresponding projection coefficient maps of a breast is shown in FIG. 1. In addition, FIG. 1h shows a plot of the magnitude of the eigen-values corresponding to the eigenvectors. More specifically, FIG. 1 shows a parametric presentation for the projection each voxel on the seven eigenstates, sorted from largest to smallest (a-g), the plot in (h) presents the associated eigenvalues magnitude in a logarithmic scale. In addition, a plot of the pattern of each eigenvector is presented in the insert of each projection map.

Most of the variability in the time courses of contrast enhancement in each pixel can be explained by using the first three eigenvectors with relatively high eigenvalues as the remaining four eigenvectors have much lower eigenvalues and their projection coefficient maps appear to reflect random noise.

FIG. 2 shows graphical representation of the three major eigenvectors which correspond to the largest eigen values of PCA results from representative breast slices in three patients diagnosed with breast cancer and breast slices in two patients diagnosed with benign breast lesions. The first two eigenvectors are similar in the cancers and benign tumors (a, b) but the third eigenvectors were separated between cancers (c) and benign tumors (d) due to their difference. Most importantly, in all cases, PCA produced three major eigenvectors that were very similar to one another for the cancer cases (FIG. 2, a-d). Consequently, a generalized eigenvector base was constructed, consisting of the median pattern derived from the 3 cancer cases. Using this new base eliminated the need to calculate the principal components of each new case from the beginning and speed-up the process of determining the eigenvectors and eigenvalues.

The distribution of the first, dominant eigenvector appeared to be related to the inhomogeneous radiofrequency (RF) and the difference in frequency due to chemical shift (such as the chemical shift difference between fat and water) and not to a characteristic of the lesion in the breast and hence, can serve to eliminate the contribution of these inhomogeneities and filter them out.

Figure 1A:
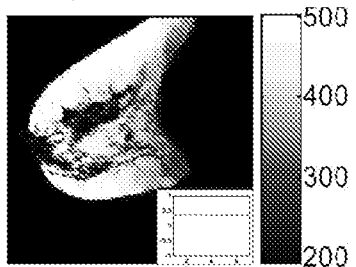
FIG. 1 shows a parametric presentation for the projection coefficients in each voxel on the seven eigenvectors and the pattern of each eigenvector, sorted from largest to smallest eigenvalues (A-G) in the breast. The plot in (H) presents the associated eigenvalues magnitude in a logarithmic scale. T1 weighted, intensity scaled magnetic resonance images recorded pre- and post contrast were used to obtain the eigenvectors and the parametric presentation of the projection coefficients
Figure 1B:
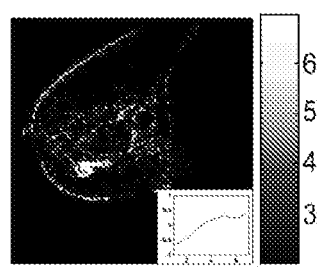
Figure 1C:
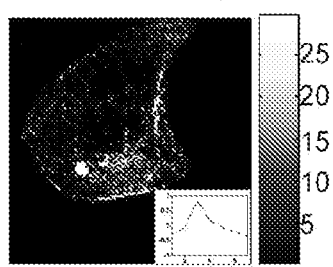
Figure 1D:
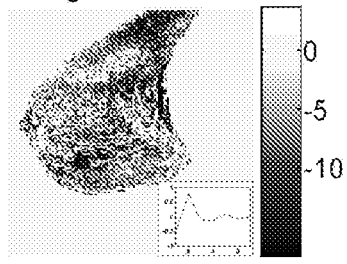
Figure 1E:
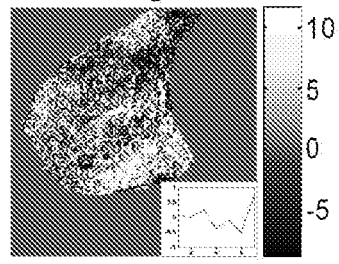
Figure 1F:
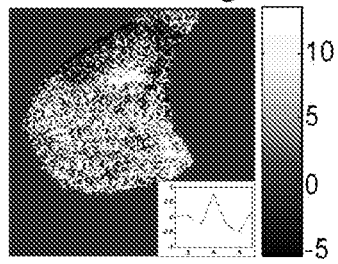
Figure 1G:
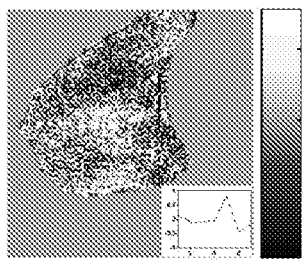
Figure 1H:
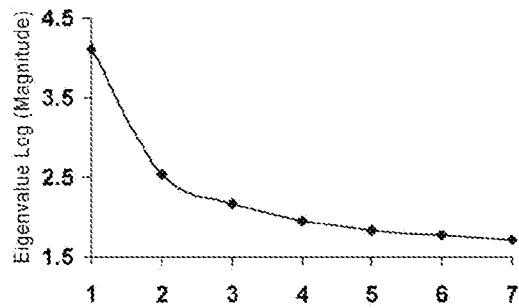
Figure 3A:
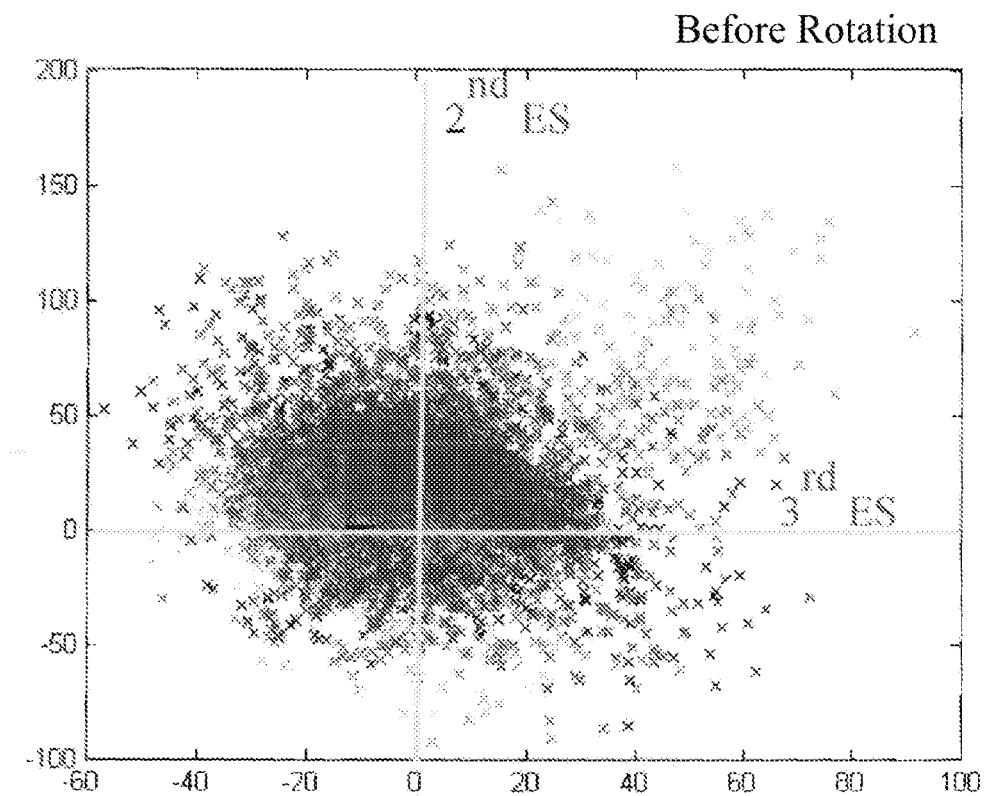
FIG. 3 shows visual compression between the PCA relevant eigen states (ES, also termed eigenvectors-EV) and the model based three time points (3TP) parameters in a breast with cancer. Each dot in the plot represents a voxel, its location indicates the values of the projection coefficients of the $2^{nd}$ and $3^{rd}$ eigenstates and its color and color intensity indicates the 3TP label. Using the most relevant eigenvector (EV) calculated in the learning step, the $2^{nd}$ (y-axis) and $3^{rd}$ (x-axis) eigenvectors (perpendicular to the 1st eigenvector in the z direction), and plotting the 3TP labeling including non-enhanced regions (black) (a) it was found that a rotation of the two eigenvectors of about 70 degrees clockwise around the 1st eigen vector creates new transformed $2^{nd}$ and $3^{rd}$ eigenvectors (REVs, also termed RESs) (b). The rotated $2^{nd}$ eigenvector reflected the change in the initial rate of enhancement and the rotated $3^{rd}$ eigenvector reflected the change in the wash-out pattern.
Figure 3B:
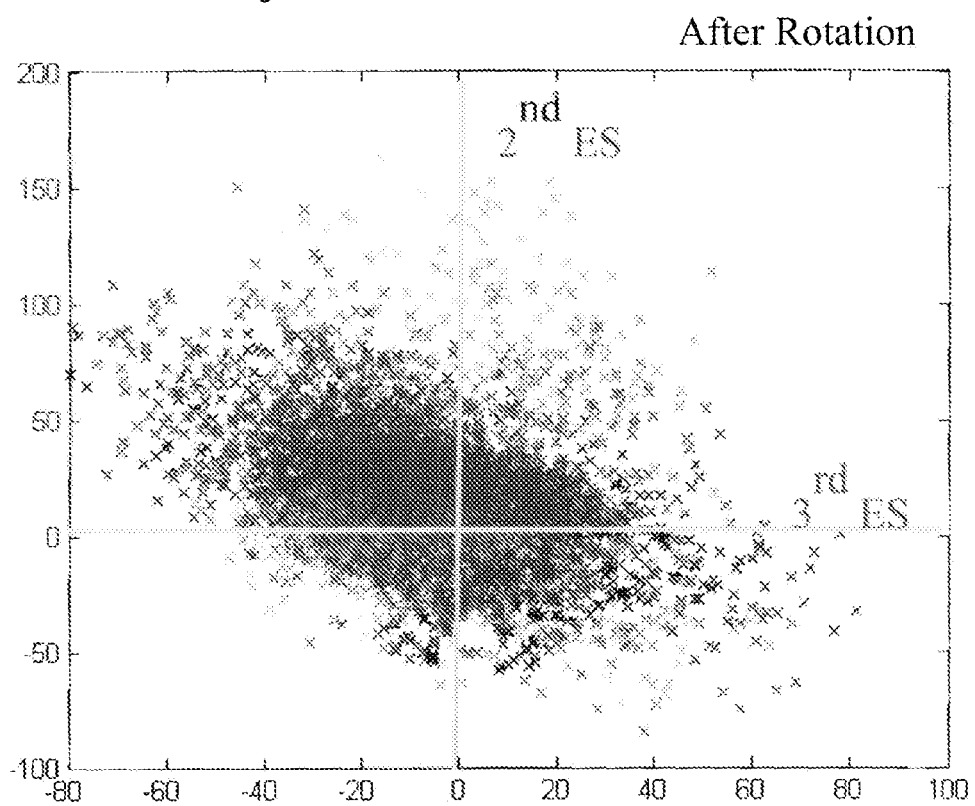

To further explore the nature of the $2^{nd}$ and $3^{rd}$ eigenvectors, yielded by the intensity-based PCA, these eigenvectors were correlated to the color-coded wash-in and wash-out patterns derived from the 3TP method, which is based on a kinetic model and may be used to distinguish between benign and malignant breast tissue. FIG. 3, shows visual compression between the two relevant eigenvectors and 3TP, each dot in the plot represents a voxel, its location indicates the values of the $2^{nd}$ and $3^{rd}$ eigenvectors coefficients and its color indicates the 3TP label. Using the eigenvectors (EV also termed eigenstates—ES) calculated in the learning step and (a) and after that base was rotated 70 degrees clockwise to create new rotated eigenvectors (also termed rotated eigenstates—RES) (b).

Figure 4:
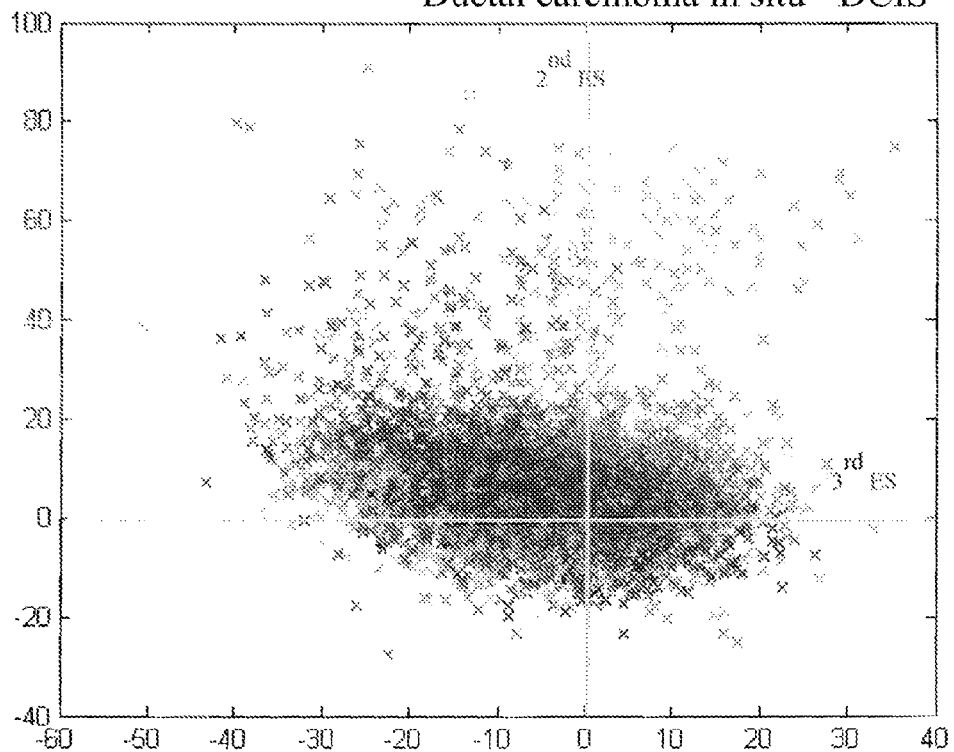
FIGS. 4 and 5 show visual compression of the rotated eigenvectors ($2^{nd}$ and $3^{rd}$ eigenvectors, also termed eigen states (ES), rotated ~70 degrees clockwise around the $1^{st}$ eigenvector) with the 3TP labeling for two cases with breast cancers, ductal carcinoma in situ and infiltrating ductal carcinoma, respectively.
Figure 5:
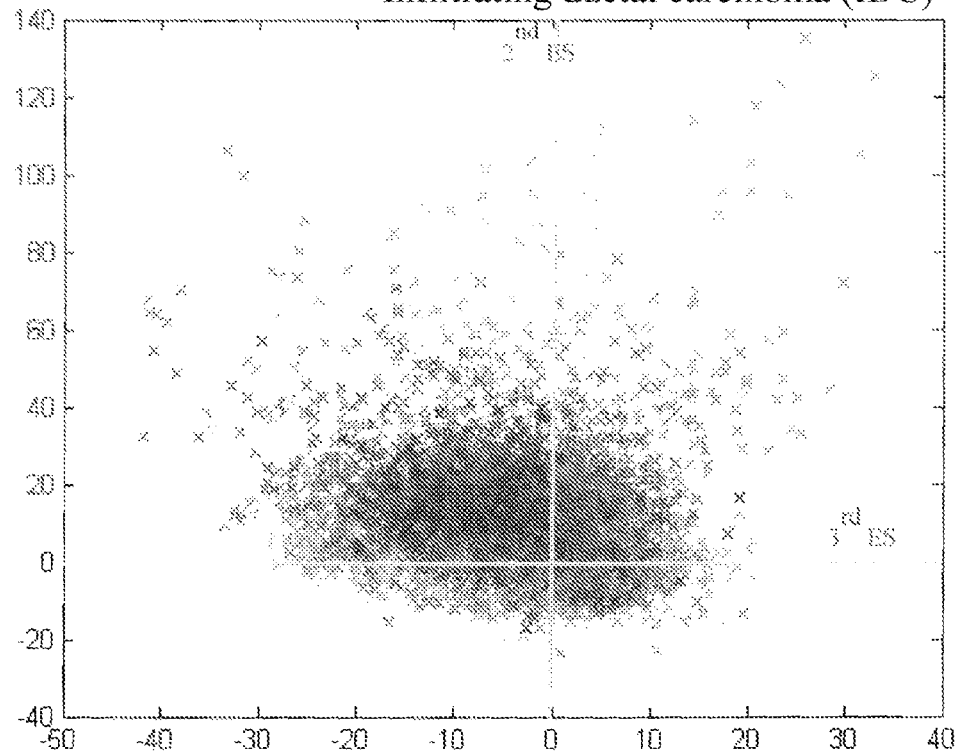
Figure 6:
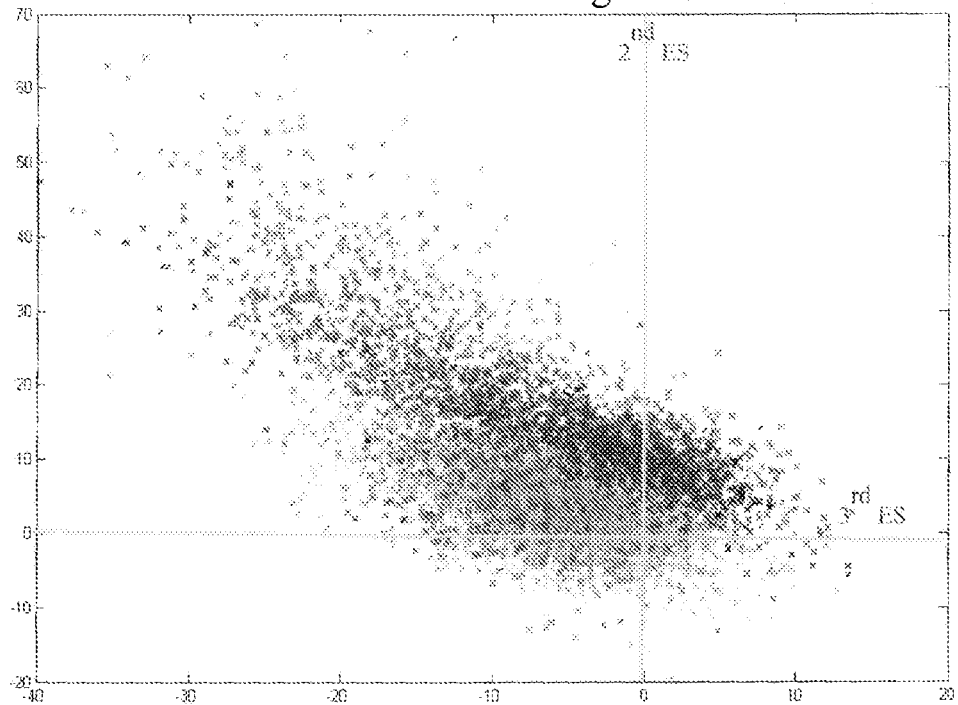
FIGS. 6 and 7 show visual compression of the rotated eigenvectors ($2^{nd}$ and $3^{rd}$ eigenvectors, also termed eigen states, rotated ~70 degrees clockwise around the $1^{st}$ eigenvector) with the 3TP labeling for 2 cases with benign breast disease, breast hamartoma and fibrocystic changes.
Figure 7:
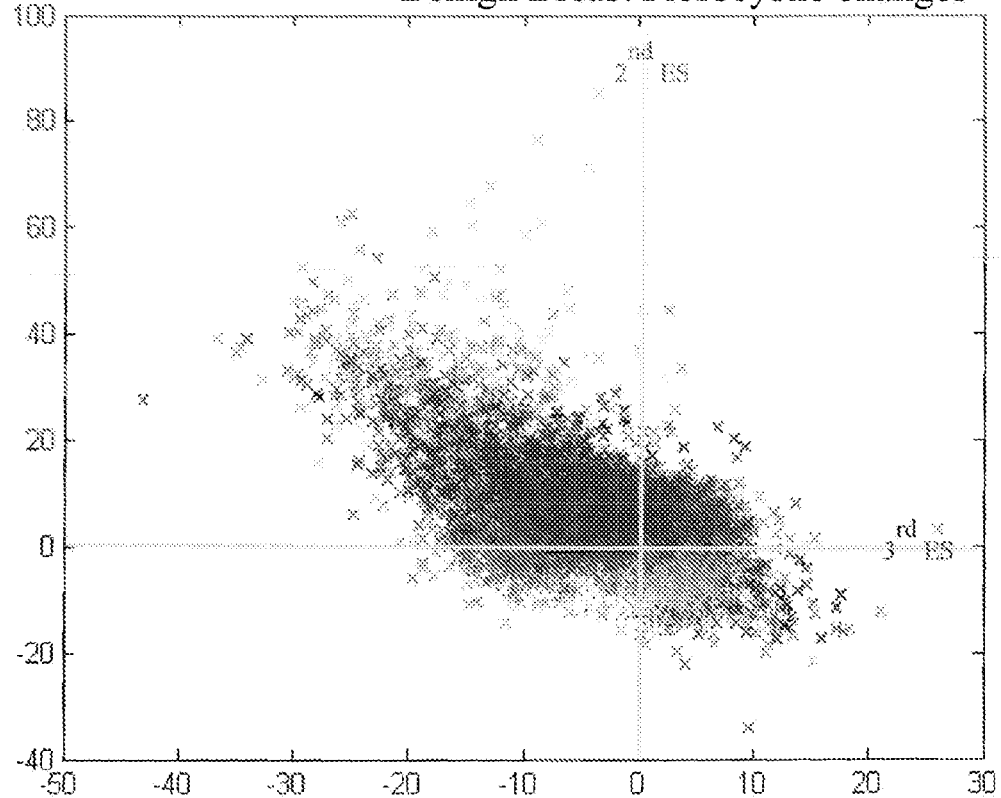

The distribution of the 3TP color-coded patterns with regard to the $2^{nd}$ and $3^{rd}$ eigenvectors was highly reproducible in all breast cancers, and revealed that rotation of these two eigenvectors by ~70 degrees clockwise around the first eigenvector yields two new rotated eigenvectors that reflect the 3TP patterns of enhancement (FIGS. 4, 5). Similarly the distribution of the 3TP color-coded patterns with regard to the $2^{nd}$ and $3^{rd}$ eigenvectors was highly reproducible in all benign breast diseases, and revealed that rotation of these two eigenvectors by ~70 degrees clockwise around the first eigenvector yields two new rotated eigenvectors that reflect the 3TP patterns of enhancement (FIGS. 6, 7). The rotated $2^{nd}$ eigenvector derived from the breast intensity scaled dataset was found to be a scaling factor related to the wash-in rate of the contrast agent as defined by the 3TP method, with its axis depicting patterns ranging from null wash-in (coded black) or dark blue green or red to fast wash-in (coded in bright—high intensity colors according to the 3TP method). The rotated $3^{rd}$ eigenvector of the intensity scaled dataset was found to be related to the wash-out pattern ranging from slow wash out (blue according to the 3TP method) to fast wash-out (red in the 3TP method) (FIGS. 3-5). It is important to note that for the benign breast disease the projection maps of the rotated $3^{rd}$ eigenvector exhibits only null or close to null intensities (FIGS. 6, 7). This can serve to differentiate the benign from cancer, as cancers exhibit in part of the regions appreciable intensity in the projection map of the rotated 3rd eigenvector.

Also there was consistent congruence between the projection mapping of the two rotated eigenvectors and the 3TP patterns indicating malignancy (FIG. 8) and those indicating benignancy (FIG. 9). FIG. 8 shows the 3TP analysis (a1; b1) and the projection coefficient maps of the 2nd (a2; b2) and 3rd (a3; b3) rotated eigenvectors in 2 representative cases (a, b). Each row shows one cancer case, white arrow indicates the lesion in the breast confirmed by histology. Each case corresponds to the same row location. In contrast, the projection maps of the rotated eigenvectors of benign breast lesions (FIG. 9) reveal that only the rotated $2^{nd}$ eigenvector shows high intensity in benign tumors whereas the rotated $3^{rd}$ eigenvector is nulled in benign breast lesions. This nulling serves to differentiate the benign from the malignant breast lesions.

The present invention provides a model-free mathematical method involving principal component analysis for analyzing and displaying dynamic contrast-enhanced magnetic resonance images of the tissue, e.g. breast, fused with pattern analysis based on a kinetic compartmental model. This hybrid methodology uniquely exploits the advantages of both approaches, and obtains a fully automated, standardized, reproducible, and potentially accurate method for diagnosing cancer, especially breast, lung, prostate or ovarian cancers.

In general, principal component analysis is considered to be a data reduction method.

Although PCA utilizes the entire dynamic data set, the resulting projection coefficient maps display decreasing signal-to-noise ratio (SNR) and therefore, only the first few need to be examined. It was found that the same three principal eigen-vectors are obtained across the breast DCE-MRI datasets (intensity scaled datasets) from 8 patients with breast cancer, suggesting that it is possible to employ a generalized set of eigen states across all breast cancer patients rather than calculating new eigenvectors for each case. It was found that for the breast for intensity scaled dataset, the $1^{st}$ eigenvector was related to an instrumental/frequency variable which did not depend on the dynamic process; Furthermore, the principal component of the $4^{th}$ to $7^{th}$ eigenvectors are believed to reflect random noise, and appeared to have no diagnostic relevance. Filtering out these eigen-vectors appeared to smooth out the data curves. This step helped to correct corruption in the intensity of the images for each time points.

Finally, only the principal component maps of the two relevant eigen-vectors ($2^{nd}$ and $3^{rd}$ eigen-vectors for intensity scaled datasets and $1^{st}$ and $2^{nd}$ eigenvectors for enhancement datasets) appeared to reflect kinetic properties of the tissue perfusion. However, the PCA method by itself does not necessarily indicate the physiological relevance of each component, and such information is critical for interpretation of the results. By correlating the two relevant PCA eigenvectors with the 3TP patterns, we showed that specific rotation of the eigenvectors yielded new rotated eigenvectors with a physiological meaning, which were found to give a better differentiation between benign and malignant breast lesions. The rotated $2^{nd}$ eigenvector in the breast reflects the wash-in rate and dominates breast malignant tissue along with the rotated $3^{rd}$ eigenvector which reflect fast wash-out. However, in benign breast tumors only the rotated $2^{nd}$ eigenvector demonstrates the lesion whereas no positive intensity or negative intensity is reflected in the rotated $3^{rd}$ eigenvector. Thus, it is possible to differentiate between benign and malignant breast lesions on the basis of the presence or absence of the high intensity regions in the projection coefficient map of the rotated $3^{rd}$ eigenvector, see in particular FIG. 22.

In many cases, magnetic resonance image analysis at pixel resolution, based on fitting the dynamic time course to an approximated model-based equation, fails as a result of low signal-to-noise ratios, or due to the inability of an approximated model to account for the complex dynamics inherent in tissue perfusion (58). Furthermore, the need to introduce an arterial input function into such models introduces limitations; a generalized input function may not be accurate for each individual case, whereas measuring this input function for each patient is difficult to implement, in a routine clinical setting. The model-free method, as well as the model-based 3TP kinetic method, do not suffer from these limitations and can successfully analyze the time courses of signal enhancement in all pixels.

The results shown herein indicate that it is possible to transform a model-free mathematical method such as PCA so that it will show high congruence with a model-based method. Although we have demonstrated standardization and reproducibility for a specific protocol in a specific tissue, it is possible to standardize the model-free analysis to any protocol, by correlating it with the kinetic model-based method which, in turn, can also be standardized across MRI scanners, T1 weighted imaging protocols, and different contrast agents. Standardization may be achieved by testing a small subgroup of cases; these results can then serve as a basis for all new cases.

Previous studies have demonstrated that high spatial resolution plays a significant role in minimizing false-negative diagnoses based on contrast-enhanced images of breast tissue, while maintaining high specificity (59). It is generally accepted that the dynamics of contrast enhancement, particularly in the wash-out phase, should be obtained at high spatial resolution, even at the expense of temporal resolution, in order to reveal tumor heterogeneity and identify "hot spots" of fast wash-out. However, whether high spatial resolution is critical for imaging the initial wash-in phase is a controversial issue.

Notably, the reduction by the PCA method to two diagnostically significant eigenvectors suggests that the patterns of enhancement can indeed be characterized by two post-contrast time points, a finding which is exploited by the 3TP method.

Twellmann et al. (31) demonstrated that PCA of DCE-MRI of the breast yields three significant eigenvectors, and suggested presenting the dynamic information by using a red-green-blue (RGB) image that fuses these three eigen states into one composite display. No relationship was found between these eigen-states and physiologically relevant patterns of contrast enhancement. However, the first eigenvector was clearly not of diagnostic value, as it predominantly depicted fatty tissue. In their protocol, two eigenvectors appeared to be sufficient for detecting malignant features of the breast, although the application taught is completely different from the present invention.

More recently, Twellmann et al. suggested the use of artificial neural network architecture to classify temporal kinetic signals in the breast (57). They then compared their results to the model-based 3TP method. Their output consisted of two parametric maps that, when taken together, indicated the presence of malignant lesions and yielded a level of accuracy similar to that of the 3TP method.

Yoo et al. (30) applied another model free method based on independent component analysis (ICA) to the characterization of DCE-MRI of the breast. Once again, it was demonstrated that two principal vectors are relevant for distinguishing to some extent between normal and malignant breast tissues; however, no correlation between these vectors and real physiological patterns of contrast enhancement was obtained.

It has been demonstrated that principal component analysis of dynamic contrast enhanced images of the breast in various patients yields very similar results when using the same imaging protocol. In this invention, PCA enables filtering out instrumental/frequency shifts artifacts and random noise, leaving only two significant eigenvectors (such as $2^{nd}$ and $3^{rd}$ eigenvectors of the intensity scaled images) for breast cancers and one significant eigenvector for benign breast lesions. These eigenvectors were transformed into rotated eigenvectors, which were then quantitatively correlated with the wash-out pattern and wash-in rate resulting from the model-based 3TP kinetic technique. The receiver operating characteristic analysis of the breast cases suggests that the projection coefficient maps of these rotated eigenvector, particularly the $2^{nd}$ rotated eigenvector of enhancement images or $3^{rd}$ rotated eigenvector of intensity scaled images, can provide a computer aided diagnostic means for diagnosing breast cancer.

The eigenvectors from different cases overlap (FIG. 2 and FIG. 18) so that one general representative eigen base can be used for all cases, without any need to calculate PCA for every new case, and no need for lesion ROI to be delineated. As previously noted, a registration tool (written in Matlab) has been used resulting in some of the dataset have offsets of several voxels between images.

As a result of the application of the present invention, there is a great time savings in processing the dataset information because the computation effort of PCA is very low compared to any classification algorithm. Thus, the processing time is reduced dramatically to about 1 sec compared to 15 min, for example, to any classification algorithm.

In addition to the detection of breast cancer as described in the foregoing, the invention has application to other forms of cancer, such as, lung, prostate, ovarian or cervical cancer.

There follows another example, of the novel image processing method of breast DCE-MRI data that integrates PCA with the model based three times point (3TP) analysis (71, 81, 82), selecting and mapping the physiologically relevant patterns of enhancement that best discriminate between benign and malignant breast lesions.

The 3TP method was already applied as a reference method for validating novel methods in detecting breast cancer by DCE-MRI (83, 84). The new processing method starts with a learning phase in which whole dynamic datasets with histology proven benign or malignant lesions were analyzed by both PCA and the 3TP method. This phase was followed by a correlation between the parametric maps of these two methods yielding a generalized, rotated eigen-vector base. This base was further employed to new cases in which unlabeled dynamic data were projected on this generalized rotated eigen-vector base to produce projection coefficient maps that help discriminate between benign and malignant breast lesions.

Patients

The results presented here were obtained using a retrospective analysis of 28 patients with 17 malignant and 15 benign lesions, all proven histologically, that participated in a clinical trial performed at the University of Wisconsin Hospital (82). The malignant lesions included 12 invasive cancers (10 infiltrating ductal carcinoma, 1 tubular and 1 tubulobular carcinoma—IDC group) and 5 ductal carcinoma in situ (DCIS). The benign lesions included 10 fibroadenoma and 5 fibrocystic changes (FCC). All patients signed a consent form approved by the University of Wisconsin institutional review board (IRB).

MR Imaging

MRI was performed at 1.5 Tesla (Signa scanner, GE Medical Systems, Waukesha, Wis.), using a dedicated phased array breast coil (MRI Devices, Waukesha, Wis.). The protocol of the DCE-MRI study was based on the 3TP method, with all instrumental parameters, time of injection, dose of contrast agent and temporal resolution described below judiciously selected using the calibration map of the 3TP method. A fast gradient-echo acquisition was employed using the following parameters: TE/TR=4.2/15 ms; flip angle 30°; FOV 16-18 cm; matrix 256×256; NEX 1.0; slice thickness 2.2-3 mm. Seven consecutive image sets of 56 slices, requiring slightly more than 2 min per acquisition were obtained in 14 min and 45 seconds. Gadodiamide (Omniscan-Nycomed Laboratories, Princeton, N.J.) was injected intravenously with an infusion pump at a dose of 0.1 mmol/kg, 3 minutes after the beginning of the scan series (1 minute after start of second scan sequence).

Data Analysis

Figure 16:
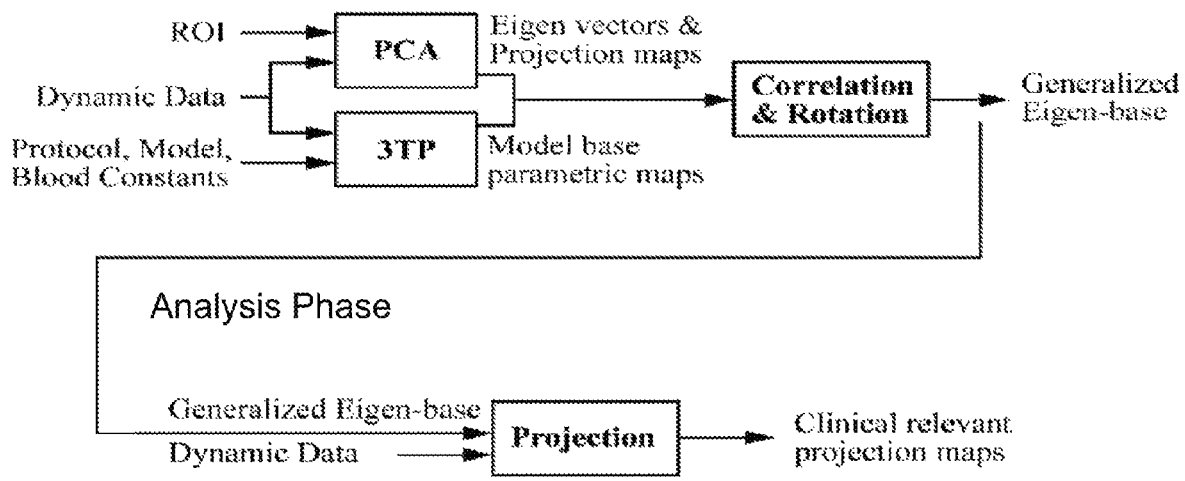
FIG. 16 shows chart flow of the main steps included in the PCA-3TP method.

For data processing, the dynamic datasets were loaded into Matlab (version 7.0.1) workspace. Enhancement images were calculated for a slice in the center of each lesion. A region of interest (ROI) of the entire breast and of the lesion in this central slice was manually demarcated (based on enhancement and the radiologist's input) (82). The processing method was composed of two phases, learning and analysis. In the learning phase, several datasets with histology proven cancer were analyzed both by principal component analysis (PCA) and by the 3TP methods. The correlation between the parametric maps of the two methods and the application of a newly developed program for achieving congruence between the parameters of both methods yielded a generalized, rotated eigen-base. In the analysis phase, unlabeled dynamic data was projected on this generalized eigen-base to produce projection coefficient maps, which assist to detect and diagnose breast cancer. The main steps in each phase are illustrated in FIG. 16 and explained below.

Learning Phase Using Enhancement Data Set:

In the learning phase, we applied principal component analysis and 3TP analysis for the group of invasive cancers (denoted IDC lesions), using the enhancement images and the lesion ROI. The characterization of the enhancement patterns, where we normalized the intensity post contrast by the pre-contrast image and calculated a dynamic enhancement data set of images, using the standard definition of enhancement: $[I(t)-I(0)]/I(0)$, where $I(0)$ and $I(t)$ represent pre-contrast and post-contrast intensity values, respectively, for the same pixel. The enhancement data set produced a common eigen-vector base. This base was then rotated after correlation with the 3TP method and a generalized rotated eigen-base was derived from the correlation of the two analysis methods.

(i) The data set was organized by manually delineating the entire breast ROI or the lesion ROI for each dataset d in a central slice that contained histologically proven cancer or benign lesion. Then, each voxel was associated with a state vector u that represents the signal enhancement values, measured at the six time points. The set of all state vectors in the ROI is defined as:

Γd={ui}, 1≤i≤N where N is the number of voxels in the ROI.

(ii) A covariance matrix of Γ, was built using the following calculation:

$$COV_{d,s} = \frac{1}{N}\sum_{u \in \Gamma}(u-\bar{u})(u-\bar{u})^T \text{ and } \bar{u} = \frac{1}{N}\sum_{u \in \Gamma} u$$

(iii) PCA calculation was performed to reduce the dimensionality of the data by mapping it to a new coordinate system of orthogonal axes. These axes are the eigen-vectors of $COV_d$ and are calculated by solving $\lambda e = COV_d e$ yielding a set of six eigen-values $\{\lambda_1, \lambda_2 \ldots \lambda_6\}$ and six eigen-vectors $E=\{e_1, e_2 \ldots e_6\}$. The eigenvectors can be indexed and sorted according to their eigenvalues, hence, $e_1$ has the largest eigenvalue and is referred as the first or dominant eigenvector.

(iv) A median base of all infiltrating ductal carcinoma cases was calculated serving as the representative normalized-eigen base (v) Spatial coefficient maps were calculated by projecting the temporal patterns on each one of the eigenvectors to produce a new scalar value. The spatial distribution of these scalar values was presented by the projection coefficient maps.

(vi) In order to relate the eigenvectors to the actual physiology of contrast enhancement, the pixel values of the first and second eigenvectors were correlated to the patterns identified by the 3TP technique using its color coding scheme. The 3TP analysis produces color-coded parametric maps accompanied by a calibration scheme that relates color hue and color intensity to physiological parameters. The correlation between the PCA and the 3TP parameters determines the degree of axes rotation of the eigenvectors to overlap with the 3TP wash-out pattern and wash-in rates, yielding a new rotated eigen-base $E_{rot}$. The rotation program for achieving optimized rotation moves on all possible angles starting with an initial guess (or with zero angle if no guess was given) and finds the angle that satisfies best the conditions set by the program for an optimal angle. The conditions (criteria) for selecting an angle are defined in the program and can be:

1. All green and red 3TP labeled voxels are positive regarding the $3^{rd}$ eigenvector axis (representing after rotation wash-out) and all blue voxels have negative value for this eigenvector axis. Similarly for enhancement data set the conditions will refer to the $2^{nd}$ eigenvector axis.

2. All red voxels and half of the green voxels with the highest intensity are positive regarding the $3^{rd}$ eigen vector axis and all blue voxels and the remaining green voxels are negative on this axis 3. Apply 1 or 2 and add another condition for the $2^{nd}$ eigenvector axis using a linear correlation fitting between the intensity and this eigenvector coefficients and choosing the angle that yields the highest correlation coefficient ($R^2$) for the linear correlation.

The flow chart for the new method is shown in FIG. 16

Analysis Phase

Projection maps of a new data set were calculated using the eigen-base $E_{rot}$, yielding parametric maps of the new rotated first and second eigenvectors. Note that after the learning phase, the analysis of a new case is time and memory efficient and neither ROI delineation nor PCA calculation is required at this phase.

Statistical Analysis

The statistical relevance of each rotated eigenvector was evaluated using Kruskal-Wallis (KW) test for significance with multiple comparisons between the various groups of breast lesion (infiltrating ductal carcinoma—IDC; ductal carcinoma in situ—DCIS; fibrocystic changes—FCC; fibroadenoma—FB), as well as with receiver operating characteristic (ROC) curves. These curves provided a graphical plot of the sensitivity vs. 1-specificity. The median or 75th percentiles of the projection coefficients of either 1st or 2nd rotated eigenvectors (obtained from enhancement data sets) served as predictors and histological labeling served as a classifier. The analysis was performed using the PROPROC software (85, 86).

FIG. 22 shows the diagnostic evaluation and validation for enhancement images set and projection coefficient maps of 1st and 2nd rotated eigenvectors (REVs) and corresponding 3TP color coded maps. Note the progressive decrease in brightness on 2nd map when advancing from IDC through DCIS to benign lesions. Median and IQR of 75th percentile values within each group is shown in the following Graphs A (FIG. 23) and B (FIG. 24).

Kruskal-Wallis (KW) test for significance with the following multiple comparisons (MC) tests are shown in the following Tables 1 and 2.

TABLE 1*

|  |  | 1st REV | prc25 | median | prc75 |
|---|---|---|---|---|---|
| KW |  | p_value | 0.0179 | 0.0006 | 4.43E−05 |
| *MC | IDC |  | a, b | a | a |
|  | DCIS |  | a, b | a, b | a, b |
|  | FCC |  | a | b | b |
|  | FB |  | b | a | a |

TABLE 2*

|  |  | 2nd REV | prc25 | median | prc75 |
|---|---|---|---|---|---|
| KW |  | p_value | 0.0268 | 0.0011 | 4.78E−05 |
| MC | IDC |  | a | a | a |
|  | DCIS |  | a | a, c | a, c |
|  | FCC |  | a | b | b |
|  | FB |  | a | b, c | b, c |

*Groups with different letters in same column are significantly different; groups sharing a letter are not significantly different.

FIG. 25 shows Receiver operating characteristic (ROC) curve analysis (PROPROC software, provided by Kurt Rossmann laboratories): The 75th percentiles of projection coefficients of either 1st or 2nd REV served as predictors and histological labeling served as a classifier. In a previous study the area under the curve (AUC), using the 3TP for differentiating benign from malignant lesions was 0.91. The following table shows the AUC for FIG. 25.

| rotated EV AUC: | Non-rotated EV AUC: |
|---|---|
| a. −0.87 | → 0.87 |
| b. −0.62 | → 0.62 |
| c. −0.93 | → 0.87 |
| d. −0.80 | → 0.77 |

| rotated EV AUC: | Non-rotated EV AUC: |
|---|---|
| a. −0.87 | → 0.87 |
| b. −0.62 | → 0.62 |
| c. −0.93 | → 0.87 |
| d. −0.80 | → 0.77 |

The type of lesion and its localization was based on histological confirmation, as well as x-ray and ultrasound mammography findings. The area under the ROC curve (AUC) is indicative of the ability of the variable to correctly separate between benign and malignant breast tissue as well as between groups such as IDC+FDCIS and FCC lesions, or IDC and FB lesion.

Figure 17:
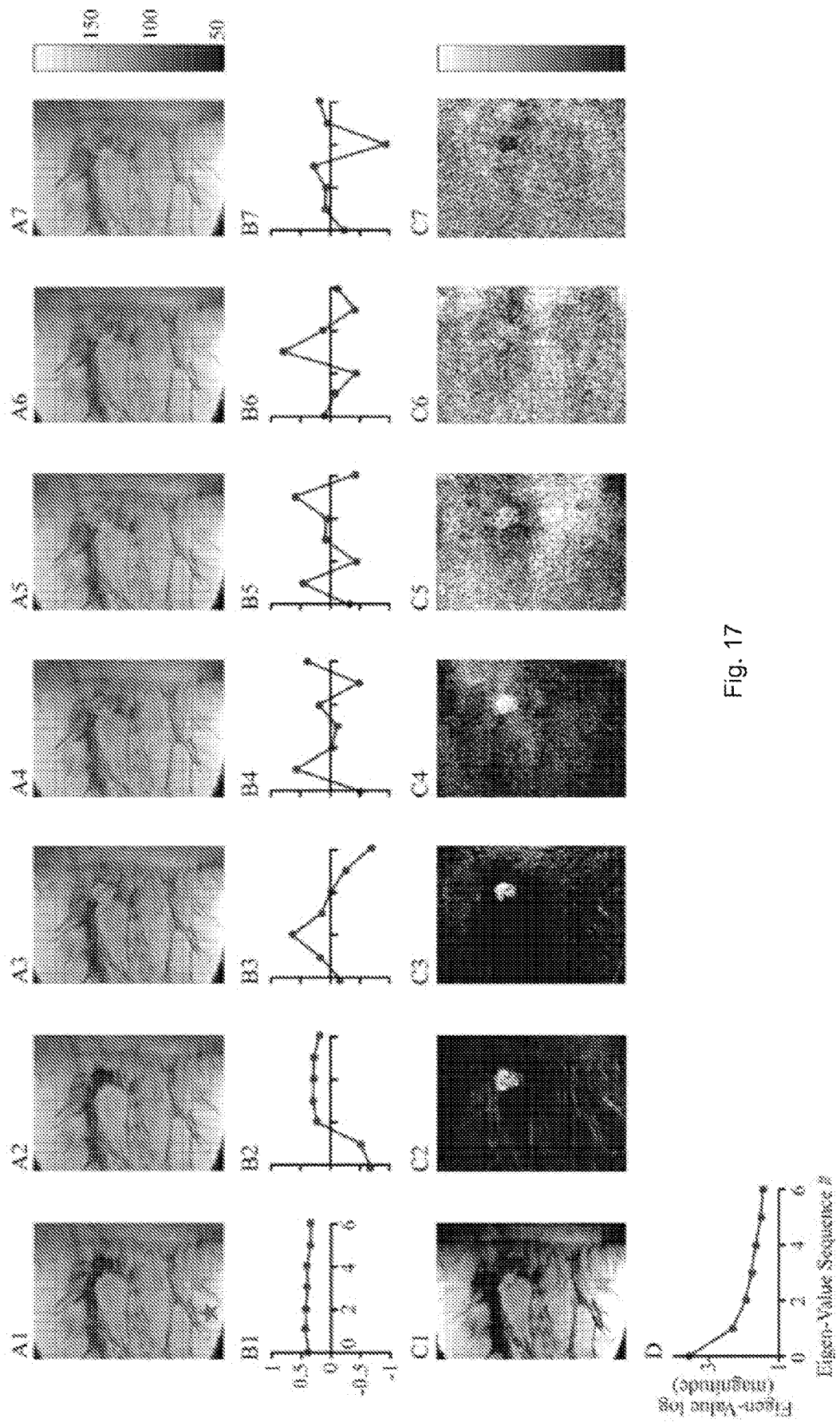
FIG. 17 shows images and PCA of a DCE-MRI of infiltrating ductal carcinoma.

A typical example of a breast DCE-MRI data set with a histologically proven IDC is demonstrated in FIG. 17, A1-A7. The MRI intensity of the lesion (pointed by the white arrow) was lower in the precontrast image (FIGS. 17, A1&2), and sharply increased, 2 min post contrast agent administration (FIG. 17, A3). In the images recorded later in time, the intensity started to slowly decline due to the clearance of the contrast agent from the tissue to the blood and eventually to the urine (FIG. 17, A4-A7). Signal intensity in the surrounding fibroglandular and fatty breast tissues only slightly increased or remained steady throughout the recording time. In all cases described inhere there were no considerable motion artifacts; however, heterogeneous intensity due to magnetic field inhomogeneities was visible in most cases (see red star).

PCA decomposition performed on raw data, namely the intensity scaled data set of images, using the entire breast ROI of a central lesion slice, yielded seven eigenvectors (FIG. 17, B1-B7). In all cases, the first eigenvector presented a flat horizontal shape (FIG. 17, B1) with a distributed projection coefficients that emerged from an instrumental artifact (FIG. 17, C1). The second and third eigenvectors (FIGS. 17, B2&B3) appeared to be indicative of the wash-in and wash-out of the contrast agent, with high coefficient values in the lesion voxels (FIGS. 17, C2&C3). The patterns in the remaining four eigenvectors were random (FIG. 17, B4-B7), and corresponded to noise on the spatial distribution maps (FIG. 17, C4-C7). A plot of the related eigen-values, showed an exponential decay in their magnitude (FIG. 17, D). The reproducibility of the first and second eigenvectors was high for all lesion types, but the third eigenvector was very consistent only for the malignant lesions. When performing the same analysis using a restricted lesion ROI, the pattern of the first eigenvector varied between the cases presumably due to the variation in the geometric location of the lesions.

We have also applied the PCA calculation, for all datasets, using dynamic enhancement images and the lesion ROI. The result was the elimination of the first eigenvector leaving only lesion related components for the first and second eigenvectors. This setup showed a repeatable and unique pattern for each lesion type (FIG. 18). In all the lesions, the first eigenvector described a sharp increase 2 min post contrast agent administration, followed by a close to plateau pattern. The malignant lesions, were characterized by a consistent, second eigenvector that also showed an initial increase followed by a consistent decrease in the consecutive points. Utilizing the reproducibly of the malignant lesion PCA de-compositions, we selected the median pattern of all IDC cases as the generalized eigenvector base (FIG. 19). Using this new base eliminated the need to re-calculate the principal components for each new case and standardized the analysis.

To determine the physiological nature of the first and second eigenvectors derived from the PCA of the enhancement images, they were correlated with the color-coded wash-in and washout labeling of the model based 3TP method (71, 81, 82). The distribution of the 3TP color-coded patterns in the plane created by the axes of the two relevant eigen vectors ($1^{st}$ and $2^{nd}$ eigenvectors for enhancement data set) was highly reproducible in all cancer and benign lesions. However, in order to get a full congruence between the eigenvectors and the 3TP labeling the eigenvectors needed to be rotated. The angle of rotation was calculated using a program for selecting the angle of rotation that optimizes for the congruency between the PCA and 3TP parameters (as indicated above). This angle was found to be ~10 degrees clockwise for the axes of the enhancement based $1^{st}$ and $2^{nd}$ eigenvectors (in exact terms 7.29 degrees according to condition 1 of the program) thus, providing a high congruency between the two methods. This revealed that for the enhancement PCA the first rotated eigenvector is a scaling parameter that depicts the extent of initial signal enhancement, which in turn relates to the wash-in rate. The second rotated eigenvector relates to the wash-out pattern of the contrast agent, with its axis depicting patterns ranging from slow wash-out (coded blue in the 3TP), to fast wash-out (coded red in the 3TP). The correlation between the 3TP and the PCA products therefore indicated that a specific rotation of the generalized eigen-base leads to their congruency (FIG. 19), and separates between the wash-in process and the washout process. This rotated eigen-base serves to analyze all new cases.

The assignment of values by PCA (after rotation) and colors by 3TP (FIG. 20) showed that infiltrating ductal carcinoma is dominated by bright green and red in the 3TP maps and high values for the first and second eigenvectors. DCIS is characterized by the dominance of light green in 3TP maps and intermediate values of PCA, the FCC group has mostly dark blue voxels in the 3TP maps with low projection values PCA and the fibroadenoma group is mostly light blue and green in 3TP maps with high values for the first eigenvector but most voxels have low values for the second eigenvector. For the distribution of projection coefficient values using the generalized rotated eigen-base. The first eigenvector has positive values for all lesions, as opposed to the surrounding tissues that have nearly zero value, showing high value for IDC and fibroadenoma, intermediate values for DCIS and the lowest values for FCC. For the second eigenvector, 15 out of the 17 malignant lesions have positive 75 percentile values, while only one of the FCC cases and three out of the ten fibroadenoma lesions were positive and therefore overlapped with the malignant cases.

Projecting a new case on the generalized rotated eigen-base produced two significant parametric maps. High projection coefficient values of the two rotated eigenvectors, particularly the second eigen-vector, co-localized with the 3TP high intensity red and green pixels that correlated with the presence of cancer (FIG. 21). For fibroadenoma and FCC lesions, the second rotated eigenvector coefficient values were similar to the surrounding tissues. This finding was further substantiated by using receiver operating characteristic (ROC) curves to investigate the diagnostic ability of the rotated eigenvectors to diagnose breast malignancy. The area under the curve (AUC) of the 75 percentile value of the first and second rotated (un-rotated values in parentheses) eigenvectors, as a diagnostic marker, yielded values of 0.93 (0.87) and of 0.94 (0.87), respectively, for differentiating between malignant and FCC lesions. However, when including all the malignant and benign lesions in the analysis, the corresponding AUC decreased to 0.55 (0.62) and 0.85 (0.77), respectively, indicating the distinct general diagnostic capacity of the second rotated eigenvector to differentiate malignant from benign breast lesions.

The invention provides a model-free method, based on principal component analysis, to evaluate dynamic contrast-enhanced magnetic resonance images of the breast. Furthermore, the invention demonstrates the means to integrate PCA with an analysis method based on a kinetic compartmental model. The purpose of the analysis was to derive pixel by pixel quantitative measurements that summarize the essence of the dynamic patterns. This process is different from other segmentation and classification (73), model free algorithms, because biological meaning is assigned for each extracted feature. The end result of the approach is a hybrid method which is fully automated, standardized, and reproducible, for detecting and differentiating between malignant and benign breast lesions.

Principal component analysis is a general method for data reduction. In the case of DCE-MRI, PCA transforms the entire data set into an ordered sequence of projection coefficient parametric maps with decreasing signal-to-noise ratio. A naive PCA of the raw images and using the entire breast ROI yielded three significant principal eigenvectors for slices that contain malignant lesions. The first eigenvector had a horizontal line shape suggesting that is unrelated to the temporal changes associated with the entrance and clearance of the contrast agent. This eigenvector is the base line intensity of each voxel and reflected the protocol dependent pre-contrast signal intensity, as well as intensity variations due to experimental inaccuracies. When performing the same analysis using the lesion ROI, the shape of the first eigenvector changed between cases and becomes dependent on the lesion's spatial location within the breast.

Applying PCA to enhancement images led to the removal of the experimental/frequency shift dependent eigenvector yielding six eigen-vectors of which only the first two appeared relevant to the lesions. The shape of the first eigenvector of enhancement data was highly reproducible for all cases, regardless of the lesion type. The shape of the second eigenvector of this data showed reproducibility only for IDC. Therefore, a generalized set was calculated of these two eigenvectors across all patients rather than calculating a new decomposition for each case. The principal component maps of the third to sixth eigenvectors suggested that they reflect a random noise process and appeared to be diagnostically insignificant. These noise related eigen-vectors can help to correct for any corruption in the time points, particularly those connected with the 3TP method, and to improve the fitting of the data to a kinetic model.

The principal component maps of the first and second eigenvectors appeared to be closely related to the kinetic information of the lesions; however, PCA by itself does not necessarily indicate the physiological relevance of each component, although such information is critical for the interpretation of the results. By correlating these two PCA eigenvectors with the 3TP parametric maps, it was shown that a rotation transformation of these eigenvectors is sufficient to reach high congruency with the parameterization generated by the 3TP model-based method. Namely, the rotated first eigenvector reflects the wash-in pattern determined by an influx transcapillary transfer constant, and the rotated second eigenvector reflects the wash-out rate determined by the outflux transcapillary transfer constant. According to the ROC analysis, the rotated second eigenvector that varies according to the extent of wash-out of the contrast agent has a highly discriminatory capacity to differentiate between malignant and benign breast lesions. This analysis also showed that the rotated first eigenvector, which varies with the wash-in rate, is capable of successfully differentiating between the malignant and FCC groups but is less efficient when adding the fibroadenoma cases into the analysis. It is important to note that although we have demonstrated standardization and reproducibility for specific scanning parameters, the hybrid method can be standardized for any T1 weighted protocol across MRI scanners, and different contrast agents. The standardization can be achieved after evaluating a small subgroup of cases that can then serve as a basis for all new cases.

The ROC analysis of all malignant vs. the FCC group shows that both the first and the second rotated eigenvectors have higher AUC values then the values of the non-rotated base demonstrating the importance of the physiological relevance to the diagnostic process. Moreover, for the differentiation between all malignant vs. all benign (FCC+fibroadenoma) lesions, the AUC of the second eigen-vector increases after rotation as opposed to the first eigenvector that show almost no correlation (AUC=0.5). Thus, rotation improves the diagnostic capacity to differentiate between malignant and FCC lesions on the basis of both the wash-in and wash-out parameters, but uses only the wash-out to separate the fibroadenoma from malignant lesions.

The specificity of DCE MRI for breast cancer diagnosis shows large heterogeneity in the literature due to variability in MR hardware and protocols, data analysis methods, as well as, verification methods and reader experience (73). On one hand, the use of arbitrary empiric enhancement parameters is highly dependent on the MRI protocol and leads to variations in the diagnostic significance of each parameter and consequently to inconsistent results and a non-standardized tool. On the other hand the kinetic modeling on a pixel by pixel basis suffers from the fact that the images are rather noisy and therefore fitting algorithms may yield false parameters as well as a long computational time. Furthermore, the two compartment model does not take into account the presence of pressure gradients (81) and interstitial diffusion that may alter the dynamic pattern, and also requires the determination of an arterial input function which is not routinely feasible.

Twellmann et al (79) showed that PCA decomposition of DCE-MRI in the breast yields three significant eigen-vectors and suggested to present the dynamic information by using RGB image that fuses these three eigenvectors. No relationship was found between these eigen-vectors and physiologically relevant patterns of contrast enhancement. In addition, the first eigenvector was not of diagnostic value. In a latter work Twellmann et al suggested the use of artificial neural network architecture for classification of the temporal kinetic signals in the breast (83), and compared their results to the 3TP analysis. Their output consisted of two parametric maps that together indicated the presence of malignant lesions and yielded a similar accuracy to that of the 3TP method. Independent component analysis also demonstrated that two principal vectors can distinguish to some degree between normal tissues and malignant cancer, however, no correlation between these vectors and real physiological patterns were obtained (78).

The hybrid method presented produced only two relevant eigenvectors for enhancement images. They were further related to the actual kinetics of contrast enhancement. This inventive method does not suffer from the above-mentioned limitations and can successfully analyze the time courses of signal enhancement in all pixels and produce maps that optimize the diagnostic capability of breast DCE-MRI.

Notably, the reduction by the PCA method to two diagnostically significant eigen-vectors suggests that the patterns of enhancement can indeed be characterized by two independent parameters, a finding which is exploited by the 3TP method.

EXEMPLARY IMPLEMENTATIONS

The present invention can be realized in hardware, software, or a combination of hardware and software. A system according to a preferred embodiment of the present invention can be realized in a centralized fashion in one computer system or in a distributed fashion where different elements are spread across several interconnected computer systems. Any kind of computer system—or other apparatus adapted for carrying out the methods described herein—is suited. A typical combination of hardware and software could be a general-purpose computer system with a computer program that, when being loaded and executed, controls the computer system such that it carries out the methods described herein.

An embodiment of the present invention can also be embedded in a computer program product, which comprises all the features enabling the implementation of the methods described herein, and which—when loaded in a computer system—is able to carry out these methods. Computer program means or computer program in the present context mean any expression, in any language, code or notation, of a set of instructions intended to cause a system having an information processing capability to perform a particular function either directly or after either or both of the following a) conversion to another language, code or, notation; and b) reproduction in a different material form.

A computer system may include, inter alia, one or more computers and at least a computer readable medium, allowing a computer system, to read data, instructions, messages or message packets, and other computer readable information from the computer readable medium. The computer readable medium may include non-volatile memory, such as ROM, Flash memory, Disk drive memory, CD-ROM, and other permanent storage. Additionally, a computer readable medium may include, for example, volatile storage such as RAM, buffers, cache memory, and network circuits. Furthermore, the computer readable medium may comprise computer readable information in a transitory state medium such as a network link and/or a network interface, including a wired network or a wireless network that allow a computer system to read such computer readable information.

Figure 11:
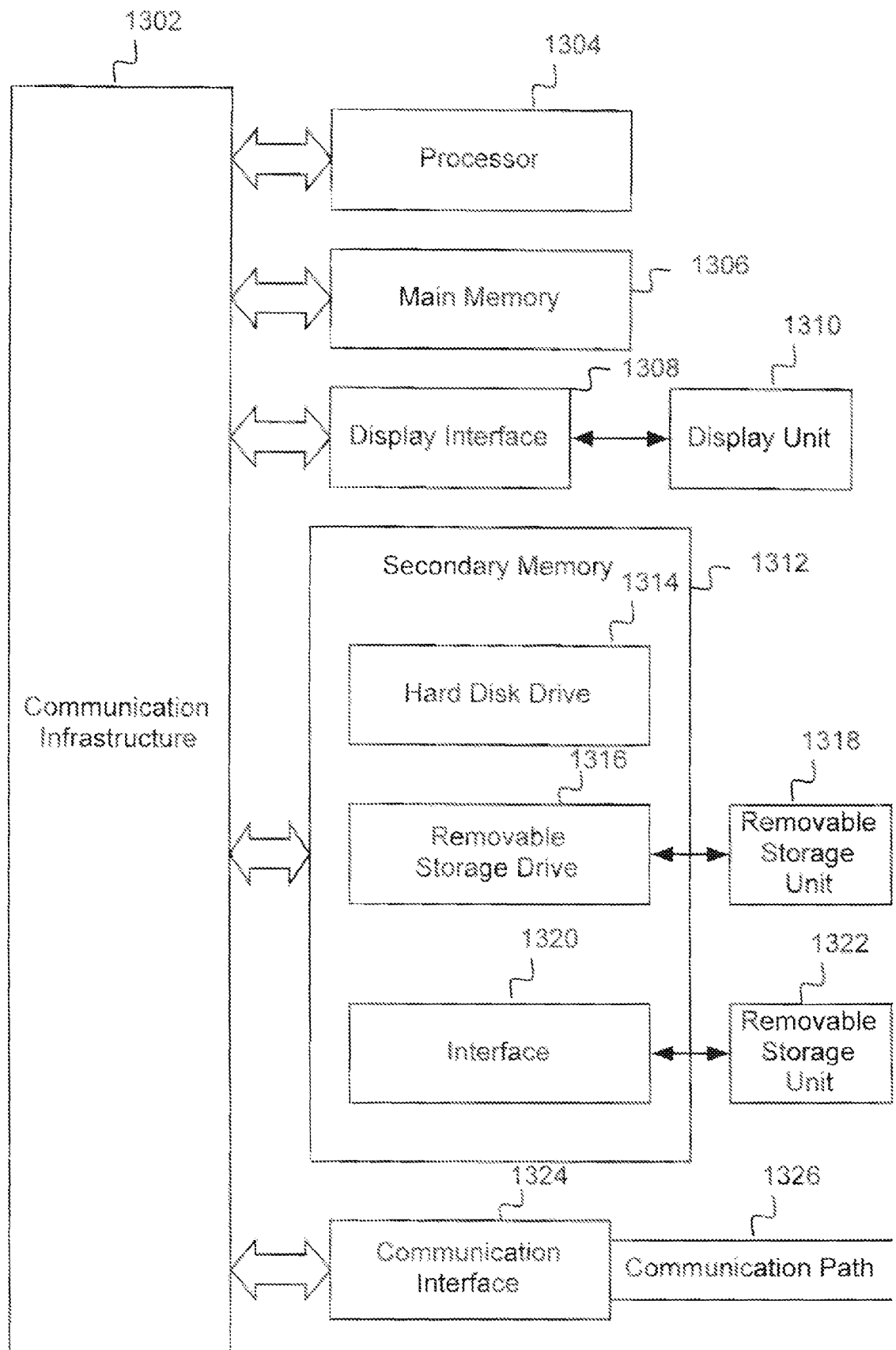
FIG. 11 is a schematic showing of a suitable computer system or apparatus for carrying out the method of the present invention.

FIG. 11 is a block diagram of a computer system useful for implementing an embodiment of the present invention. The computer system includes one or more processors, such as processor 1304. The processor 1304 is connected to a communication infrastructure 1302 (e.g., a communications bus, cross-over bar, or network). Various software embodiments are described in terms of this exemplary computer system. After reading this description, it will become apparent to a person of ordinary skill in the relevant art(s) how to implement the invention using other computer systems and/or computer architectures.

The computer system can include a display interface 1308 that forwards graphics, text, and other data from the communication infrastructure 1302 (or from a frame buffer not shown) for display on the display unit 1310. The computer system also includes a main memory 1306, preferably random access memory (RAM), and may also include a secondary memory 1312. The secondary memory 1312 may include, for example, a hard disk drive 1314 and/or a removable storage drive 1316, representing a floppy disk drive, a magnetic tape drive, an optical disk drive, and more. The removable storage drive 1316 reads from and/or writes to a removable storage unit 1318 in a manner well known to those having ordinary skill in the art. Removable storage unit 1318 represents a floppy disk, magnetic tape, optical disk, and more which is read by and written to by removable storage drive 1316. As will be appreciated, the removable storage unit 1318 includes a computer usable storage medium having stored therein computer software and/or data.

In alternative embodiments, the secondary memory 1312 may include other similar means for allowing computer programs or other instructions to be loaded into the computer system. Such means may include, for example, a removable storage unit 1322 and an interface 1320. Examples of such may include a program cartridge and cartridge interface (such as that found in video game devices), a removable memory chip (such as an EPROM, or PROM) and associated socket, and other removable storage units 1322 and interfaces 1320 which allow software and data to be transferred from the removable storage unit 1322 to the computer system.

The computer system may also include a communications interface 1324. Communications interface 1324 allows software and data to be transferred between the computer system and external devices. Examples of communications interface 1324 may include a modem, a network interface (such as an Ethernet card), a communications port, a PCMCIA slot and card, and more Software and data transferred via communications interface 1324 are in the form of signals which may be, for example, electronic, electromagnetic, optical, or other signals capable of being received by communications interface 1324. These signals are provided to communications interface 1324 via a communications path (i.e., channel)

1326. This channel 1326 carries signals and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory 1306 and secondary memory 1312, removable storage drive 1316, a hard disk installed in hard disk drive 1314, and signals. These computer program products are means for providing software to the computer system. The computer readable medium allows the computer system to read data, instructions, messages or message packets, and other computer readable information from the computer readable medium. The computer readable medium, for example, may include non-volatile memory, such as Floppy, ROM, Flash memory, Disk drive memory, CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information.

Computer programs (also called computer control logic) are stored in main memory 1306 and/or secondary memory 1312. Computer programs may also be received via communications interface 1324. Such computer programs, when executed, enable the computer system to perform the features of the present invention as discussed herein. In particular, the computer programs, when executed, enable the processor 1304 to perform the features of the computer system. Accordingly, such computer programs represent controllers of the computer system.

To summarize the inventive concept, following the PCA processing of the images, there is a quantitative correlation with a model based method which selects an optimized rotation angle and only then a rotation is made of the PCA eigenvectors, and then projection coefficient maps are made. The correlation between the eigenvectors and, for example, the 3TP labeling (model based method or technique) followed by the rotation according to the optimized rotation angle provides already the ability of each eigenvector to represent a physiological parameter (for example wash-in and wash-out). The projection maps, displayed or printed, give the capability to localize where the projection coefficients of each eigenvector are high. Thereby, one can identify the presence of a lesion (detection) from the high projection coefficient of the rotated eigenvector that correlates with wash-in and from the presence of high values of projection coefficient of the rotated eigenvector that correlates with wash-out, one can differentiate benign from malignant breast tissue.

A summary of the inventive concept follows:
1. Obtain a set of dynamic contrast enhanced images of a tissue, organ or a whole region in the body where there might be abnormality.
2. The dynamic images usually are obtained in an intensity scale and can be termed "intensity scaled data-set".
3. The Intensity scaled data-set may need registration one to another—such as, for translational motion.
4. The dynamic intensity data set (without or better after registration) is converted to an enhancement data-set, normalizing the post-contrast images to the pre-contrast image using the standard definition of enhancement: $[I(t)-I(0)]/I(0)$, where $I(0)$ and $I(t)$ represent pre-contrast and post-contrast intensity values, respectively, for the same pixel.
5. The ROI of the whole breast is marked manually on the set of images that are going to be analyzed. In the learning step, where one uses data with histological confirmation, a slice is chosen for the dynamic data set that includes the lesion and is marked the ROI of the lesion manually.
6. PCA analysis can be performed on a. the intensity scaled data-set for the breast ROI, b. on the enhancement data-set for the breast ROI and c. on the enhancement data set for the lesion ROI in the learning phase.
7. The number of eigenvectors in each PCA is the number of time points. For t time points one gets t eigenvectors for intensity scaled data set and t−1 eigenvectors for enhancement data set.
8. We found that for PCA of intensity scaled images the first eigenvector is not related to the tissue and reflects instrumental artifacts. In the case of the breast this artifact is not time dependent, and therefore, does not corrupt the dynamic behavior. We can eliminate this "artifact" by using enhancement data-set which takes care of eliminating this artifact.
9. The 2nd and $3^{rd}$ eigenvectors in the PCA of intensity scaled data-set are similar in their pattern to the $1^{st}$ and $2^{nd}$ eigen vectors in the PCA of enhancement data set (they are not believed to be the same, but the overall shape of the eigen vectors is similar).
10. The $1^{st}$ and $2^{nd}$ eigenvector of PCA of enhancement data set over breast ROI are similar to the $1^{st}$ and $2^{nd}$ eigenvectors of enhancement data set over breast lesion ROI, however, there is much more variation among different cases when a whole breast ROI is used. The lesion ROI makes the patterns more similar, and therefore in the learning phase one uses these images and ROI to create a coherent eigenvector basis, using one type of lesions-cancer.
11. The 4-7 eigenvectors in the intensity scaled data set and the 3-6 eigen vectors in the enhancement data set have the appearance of noise—not using them presents the dimensionality reduction capacity of PCA
12. The correlation of the relevant two eigenvectors with 3TP is performed with those obtained from the intensity scaled images or with those obtained from the enhancement images, However, the rotation angle is not the same and will depend on the set (for the intensity scaled set it was 70 degrees and for the enhancement 10 degrees which shows that there is a difference in the PCA of the two data sets, which after rotation cancels out).
13. From the diagnostic aspect for differentiating benign from malignant breast lesions, the fused PCA-3TP method is better than the PCA alone as indicated by the ROC analysis. Also the standardization of the PCA by correlation with 3TP and rotation ensures that the final PCA will not include "instrumental" or other "artifacts" by filtering an instrumental dependent eigenvector in intensity scaled images or use enhancement datasets. In general, when the signal to noise ratio of the images is poor, intensity scaled images are preferable.
14. Once the rotated eigenvector base is obtained for a certain MRI protocol, one can apply this base to obtain projection maps of the two relevant eigenvectors in a new data set and get the means (or percentiles) for localizing the region of the lesion—namely detection (based on where there is a high intensity of the $1^{st}$ relevant eigenvector) and to differentiate between benign and malignant lesions based on the second relevant eigenvector (high intensity of this eigenvector is typical to cancers, null or negative intensity is a benign lesion).

Although the invention has been described and illustrated in terms of specific embodiments, changes and modifications by artisans of ordinary skill in the art are deemed to fall within the scope of the appended claims.

REFERENCES

1. Axel, L. Cerebral blood flow determination by rapid-sequence computed tomography: theoretical analysis. Radiology, 137: 679-686, 1980.
2. Kety, S. S. Measurement of local contribution within the brain by means of inert, diffusible tracers; examination of the theory, assumptions and possible sources of error. Acta Neurol Scand Suppl, 14: 20-23, 1965.
3. Kety, S. S. Observations on the validity of a two compartmental model of the cerebral circulation. Acta Neurol Scand Suppl, 14: 85-87, 1965.
4. Choyke, P. L., Dwyer, A. J., and Knopp, M. V. Functional tumor imaging with dynamic contrast-enhanced magnetic resonance imaging. J Magn Reson Imaging, 17: 509-520, 2003.
5. Collins, D. J. and Padhani, A. R. Dynamic magnetic resonance imaging of tumor perfusion. Approaches and biomedical challenges. IEEE Eng Med Biol Mag, 23: 65-83, 2004.
6. Kaiser, W. A. MRM promises earlier breast cancer diagnosis. Diagn Imaging (San Franc), 14: 88-93, 1992.
7. Kuhl, C. K., Mielcareck, P., Klaschik, S., Leutner, C., Wardelmann, E., Gieseke, J., and Schild, H. H. Dynamic breast MR imaging: are signal intensity time course data useful for differential diagnosis of enhancing lesions? Radiology, 211: 101-110, 1999.
8. Kuhl, C. K. and Schild, H. H. Dynamic image interpretation of MRI of the breast. J Magn Reson Imaging, 12: 965-974, 2000.
9. Schaefer, J. F., Vollmar, J., Schick, F., Vonthein, R., Seemann, M. D., Aebert, H., Dierkesmann, R., Friedel, G., and Claussen, C. D. Solitary pulmonary nodules: dynamic contrast-enhanced MR imaging—perfusion differences in malignant and benign lesions. Radiology, 232: 544-553, 2004.
10. Futterer, J. J., Heijmink, S. W., Scheenen, T. W., Veltman, J., Huisman, H. J., Vos, P., Hulsbergen-Van de Kaa, C. A., Witjes, J. A., Krabbe, P. F., Heerschap, A., and Barentsz, J. O. Prostate cancer localization with dynamic contrast-enhanced MR imaging and proton MR spectroscopic imaging. Radiology, 241: 449-458, 2006.
11. Padhani, A. R., Gapinski, C. J., Macvicar, D. A., Parker, G. J., Suckling, J., Revell, P. B., Leach, M. O., Dearnaley, D. P., and Husband, J. E. Dynamic contrast enhanced MRI of prostate cancer: correlation with morphology and tumour stage, histological grade and PSA. Clin Radiol, 55: 99-109, 2000.
12. Padhani, A. R., Harvey, C. J., and Cosgrove, D. O. Angiogenesis imaging in the management of prostate cancer. Nat Clin Pract Urol, 2: 596-607, 2005.
13. Kuhl, C. K., Schild, H. H., and Morakkabati, N. Dynamic bilateral contrast-enhanced MR imaging of the breast: trade-off between spatial and temporal resolution. Radiology, 236: 789-800, 2005.
14. Bloch, B. N., Helbich, T., and Heinz-Peer, G. [Prostatic carcinoma: current status of diagnostic imaging]. Wien Med Wochenschr Suppl 89-91, 2002.
15. Furman-Haran, E., Grobgeld D., Kelcz, F., and Degani, H. The critical role of spatial resolution in dynamic contrast enhanced breast MRI". J Magn. Res. Imaging, 13: 862-867, 2001.
16. Degani, H., Gusis, V., Weinstein, D., Fields, S., and Strano, S. Mapping pathophysiological features of breast tumors by MRI at high spatial resolution. Nat Med, 3: 780-782, 1997.
17. Kelcz, F., Furman-Haran, E., Grobgeld, D., and Degani, H. Clinical testing of high-spatial-resolution parametric contrast-enhanced MR imaging of the breast. AJR Am J Roentgenol, 179: 1485-1492, 2002.
18. Evelhoch, J., Garwood, M., Vigneron, D., Knopp, M., Sullivan, D., Menkens, A., Clarke, L., and Liu, G. Expanding the use of magnetic resonance in the assessment of tumor response to therapy: workshop report. Cancer Res, 65: 7041-7044, 2005.
19. Evelhoch, J. L. Key factors in the acquisition of contrast kinetic data for oncology. J Magn Reson Imaging, 10: 254-259, 1999.
20. Jeswani, T. and Padhani, A. R. Imaging tumour angiogenesis. Cancer Imaging, 5: 131-138, 2005.
21. Leach, M. O., Brindle, K. M., Evelhoch, J. L., Griffiths, J. R., Horsman, M. R., Jackson, A., Jayson, G. C., Judson, I. R., Knopp, M. V., Maxwell, R. J., McIntyre, D., Padhani, A. R., Price, P., Rathbone, R., Rustin, G. J., Tofts, P. S., Tozer, G. M., Vennart, W., Waterton, J. C., Williams, S. R., and Workman, P. The assessment of antiangiogenic and antivascular therapies in early-stage clinical trials using magnetic resonance imaging: issues and recommendations. Br J Cancer, 92: 1599-1610, 2005.
22. Padhani, A. R. MRI for assessing antivascular cancer treatments. Br J Radiol, 76 Spec No 1: S60-80, 2003.
23. Jemal, A., Murray, T., Ward, E., Samuels, A., Tiwari, R. C., Ghafoor, A., Feuer, E. J., and Thun, M. J. Cancer statistics, 2005. CA Cancer J Clin, 55: 10-30, 2005.
24. Parker, G. J. and Tofts, P. S. Pharmacokinetic analysis of neoplasms using contrast-enhanced dynamic magnetic resonance imaging. Top Magn Reson Imaging, 10: 130-142, 1999.
25. Tofts, P. S. Modeling tracer kinetics in dynamic Gd-DTPA MR imaging. J Magn Reson Imaging, 7: 91-101, 1997.
26. Tofts, P. S. Standardisation and optimisation of magnetic resonance techniques for multicentre studies. J Neurol Neurosurg Psychiatry, 64 Suppl 1: S37-43, 1998.
27. Tofts, P. S., Brix, G., Buckley, D. L., Evelhoch, J. L., Henderson, E., Knopp, M. V., Larsson, H. B., Lee, T. Y., Mayr, N. A., Parker, G. J., Port, R. E., Taylor, J., and Weisskoff, R. M. Estimating kinetic parameters from dynamic contrast-enhanced T(1)-weighted MRI of a diffusable tracer: standardized quantities and symbols. J Magn Reson Imaging, 10: 223-232, 1999.
28. Galbraith, S. M., Lodge, M. A., Taylor, N. J., Rustin, G. J., Bentzen, S., Stirling, J. J., and Padhani, A. R. Reproducibility of dynamic contrast-enhanced MRI in human muscle and tumours: comparison of quantitative and semi-quantitative analysis. NMR Biomed, 15: 132-142, 2002.
29. Jesberger, J. A., Rafie, N., Duerk, J. L., Sunshine, J. L., Mendez, M., Remick, S. C., and Lewin, J. S. Model-free parameters from dynamic contrast-enhanced-MRI: sensitivity to EES volume fraction and bolus timing. J Magn Reson Imaging, 24: 586-594, 2006.
30. Yoo, S. S., Gil Choi, B., Han, J. Y., and Hee Kim, H. Independent component analysis for the examination of dynamic contrast-enhanced breast magnetic resonance imaging data: preliminary study. Invest Radiol, 37: 647-654, 2002.

31. Twellmann, T., Saalbach, A., Gerstung, O., Leach, M. O., and Nattkemper, T. W. Image fusion for dynamic contrast enhanced magnetic resonance imaging. Biomed Eng Online, 3: 35, 2004.
32. Walker-Samuel, S., Leach, M. O., and Collins, D. J. Evaluation of response to treatment using DCE-MRI: the relationship between initial area under the gadolinium curve (IAUGC) and quantitative pharmacokinetic analysis. Phys Med Biol, 51: 3593-3602, 2006.
33 to 52 (No reference)
53. Cootes, T., Hill, A., Taylor, C., and Haslam, J. The use of active shape models for locating structures in medical images. Image and Vision Computing, 12: 355-365, 1994.
54. Jolliffe, I. T. Principal Component Analysis. Springer-Verlag, 1989.
55. Razifar, P., Axelsson, J., Schneider, H., Langstrom, B., Bengtsson, E., and Bergstrom, M. A new application of pre-normalized principal component analysis for improvement of image quality and clinical diagnosis in human brain PET studies—clinical brain studies using [11C]-GR205171, [11C]-L-deuterium-deprenyl, [11C]-5-Hydroxy-L-Tryptophan, [11C]-L-DOPA and Pittsburgh Compound-B. Neuroimage, 33: 588-598, 2006.
56. Furman-Haran, E. and Degani, H. Parametric analysis of breast MRI. J Comput Assist Tomogr, 26: 376-386, 2002.
57. Twellmann, T., Lichte, O., and Nattkemper, T. W. An adaptive tissue characterization network for model-free visualization of dynamic contrast-enhanced magnetic resonance image data. IEEE Trans Med Imaging, 24: 1256-1266, 2005.
58. Hassid, Y., Furman-Haran, E., Margalit, R., Eilam, R., and Degani, H. Noninvasive magnetic resonance imaging of transport and interstitial fluid pressure in ectopic human lung tumors. Cancer Res, 66: 4159-4166, 2006.
59. Furman-Haran, E., Grobgeld, D., Kelcz, F., and Degani, H. Critical role of spatial resolution in dynamic contrast-enhanced breast MRI. J Magn Reson Imaging, 13: 862-867, 2001.
60. to 62 (No Reference)
63 Shapiro, S., Coleman, E. A., Broeders, M., Codd, M., de Koning, H., Fracheboud, J., Moss, S., Paci, E., Stachenko, S., and Ballard-Barbash, R. "Breast cancer screening programmes in 22 countries: current policies, administration and guidelines, International Breast Cancer Screening Network (IBSN) and the European Network of Pilot Projects for Breast Cancer Screening" Int J Epidemiol 27, 735-742 (1998)
64. Green, B. B. and Taplin, S. H. "Breast cancer screening controversies" J Am Board Fam Pract 16, 233-241 (2003)
65. Blanks, R. G., Moss, S. M., McGahan, C. E., Quinn, M. J., and Babb, P. J. "Effect of NHS breast screening programme on mortality from breast cancer in England and Wales, 1990-8: comparison of observed with predicted mortality" Bmj 321, 665-669 (2000)
66. Jatoi, I. and Miller, A. B. "Why is breast-cancer mortality declining?" Lancet Oncol 4, 251-254 (2003)
67. El Yousef, S. J., Duchesneau, R. H., Alfidi, R. J., Haaga, J. R., Bryan, P. J., and LiPuma, J. P. "Magnetic resonance imaging of the breast. Work in progress" Radiology 150, 761-766 (1984)
68. Kaiser, W. A. and Zeitler, E. "MR imaging of the breast: fast imaging sequences with and without Gd-DTPA. Preliminary observations" Radiology 170, 681-686 (1989)
69. Morris, E. A. "Diagnostic breast MR imaging: current status and future directions" Radiol Clin North Am 45, 863-880vii (2007)
70. Vandermeer, F. Q. and Bluemke, D. A. "Breast MRI: state of the art" Cancer Invest 25, 384-392 (2007)
71. Degani, H., Gusis, V., Weinstein, D., Fields, S., and Strano, S. "Mapping pathophysiological features of breast tumors by MRI at high spatial resolution" Nature Med 3, 780-782 (1997)
72. Furman-Haran, E., Grobgeld, D., Kelcz, F., and Degani, H. "Critical role of spatial resolution in dynamic contrast-enhanced breast MRI" J. Magn. Reson. Imaging 13, 862-867 (2001)
73 Henderson, E., Rutt, B. K., and Lee, T. Y. "Temporal sampling requirements for the tracer Ikeda, D. M. "Progress report from the American College of Radiology Breast MR Imaging Lexicon Committee" Magn Reson Imaging Clin N Am 9, 295-302vi (2001)
75. Morris, E. A. "Breast MR imaging lexicon updated" Magn Reson Imaging Clin N Am 14, 293-303v (2006)
76. Kuhl, C. "The current status of breast MR imaging. Part I. Choice of technique, image interpretation, diagnostic accuracy, and transfer to clinical practice" Radiology 244, 356-378 (2007)
77. Furman-Haran, E. and Degani, H. "Parametric analysis of breast MRI" J. Comput. Assist. Tomogr 26, 376-386 (2002)
78. Yoo, S. S., Gil Choi, B., Han, J. Y., and Hee Kim, H. "Independent component analysis for the examination of dynamic contrast-enhanced breast magnetic resonance imaging data: preliminary study" Invest Radiol 37, 647-654 (2002)
79. Twellmann, T., Saalbach, A., Gerstung, O., Leach, M. O., and Nattkemper, T. W. "Image fusion for dynamic contrast enhanced magnetic resonance imaging" Biomed Eng Online 3, 35 (2004)
80. Eyal, E. and Degani, H. "Model-based and model-free parametric analysis of breast dynamic-contrast-enhanced MRI" NMR Biomed, (2007)
81. Furman-Haran, E., Grobgeld, D., Margalit, R., and Degani, H. "Response of MCF7 human breast cancer to tamoxifen: evaluation by the three-time-point, contrast-enhanced magnetic resonance imaging method" Clin Cancer Res 4, 2299-2304 (1998)
82. Kelcz, F., Furman-Haran, E., Grobgeld, D., and Degani, H. "Clinical testing of high-spatial-resolution parametric contrast-enhanced MR imaging of the breast" Am. J. Roentgenol. 179, 1485-1492 (2002)
83. Twellmann, T., Lichte, O., and Nattkemper, T. W. "An adaptive tissue characterization network for model-free visualization of dynamic contrast-enhanced magnetic resonance image data" IEEE Trans Med Imaging 24, 1256-1266 (2005)
84. Lee, S. H., Kim, J. H., Kim, K. G., Park, J. S., Park, S. J., and Moon, W. K. "Optimal Clustering of Kinetic Patterns on Malignant Breast Lesions: Comparison between K-means Clustering and Three-time-points Method in Dynamic Contrast-enhanced MRI" Conf Proc IEEE Eng Med Biol Soc 1, 2089-2093 (2007)
85. Pesce, L. L. and Metz, C. E. "Reliable and computationally efficient maximum-likelihood estimation of proper binormal ROC curves" Acad Radiol 14, 814-829 (2007)
86. "http://www-radiology.uchicago.edu/krl"

What is claimed is:
1. A method for computer-aided diagnosis of cancer comprising the steps of:
   a) performing dynamic contrast-enhanced magnetic resonance imaging on a tissue, organ or whole region of a body (ROI) where there might be an abnormality and obtaining a first dataset of images;

b) performing a learning step using a second preselected dataset of images with histological confirmance of at least one type of tissue lesion by (i) conducting principal component analysis on the portion of said preselected data correlated with the tissue lesion, (ii) obtaining by principal component analysis a plurality of eigenvectors, (iii) performing analysis of at least the portion of the preselected data by 3TP algorithm labeling to obtain an output of color hue/color intensity coded images with respect to transcapillary transfer constants and extracellular extravascular volume fraction indicative of the at least one type of tissue lesion wherein color intensity reflects changes in signal intensity between the $1^{st}$ time point (pre-contrast) and the $2^{nd}$ time point (termed "wash-in rate"), and color hue reflects changes in signal intensity between the $2^{nd}$ time point and the $3^{rd}$ time point (termed "wash-out pattern") according to one preselected color for increased signal intensity, a second preselected color for no significant change, and a third preselected color for decrease in signal intensity, and (iv) manipulating the x and y axes of the eigenvectors around their z-axis to determine a median rotated eigenvector base $E_{rot}$ for at least two eigenvectors, one of which correlates with the wash-in rate and the other of which correlates with wash-out pattern of the 3TP algorithm labeling color hue/color intensity coded images;

c) performing principal component analysis on the first dataset of images according to the algorithm $P_{d,s} = \Gamma E_{rot}^{-1}$ wherein $P_{d,s}$ is the projection of the input data (dataset $\Gamma$) on $E_{rot}$ yielding projection coefficient maps of the rotated at least two eigenvectors and enabling detection of a cancerous lesion by a high intensity appearing in the projection coefficient map of the rotated eigenvector correlated with wash-in rate and by a high intensity appearing in the projection coefficient map of the rotated eigenvector correlated with wash-out pattern, and distinguishing between cancerous lesions and benign lesions by each benign lesion appearing in the projection coefficient map of the rotated eigenvector correlated with wash-out pattern showing as a null or negative intensity; and d) outputting the projection coefficient maps of the rotated at least two eigenvectors.

2. The method of claim 1 including the further steps of converting the obtained first dataset of images to an enhancement dataset of images by normalizing post-contrast images to pre-contrast images using standard definition of enhancement, $[I(t)-I(0)/I(0)$, where I(0) and (t) pre-contrast and post-contrast intensity values, respectively, for the same pixel; and carrying out step c) using the enhancement dataset of images.

3. The method of claim 1 wherein the first color is blue, the second color is green and the third color is red.

4. The method of claim 1 wherein the projection coefficient maps are displayed.

5. The method of claim 1 including the further step of maintaining the eigenvectors orthongal when rotated.

6. A non-transitory computer readable storage performing a computer-aided diagnosis of cancer by performing dynamic contrast-enhanced magnetic resonance imaging on a tissue, organ or whole region of a body (ROI) where there might be an abnormality and obtaining a first dataset of images; performing a learning step using a second preselected dataset of images with histological confirmance of at least one type of tissue lesion by (i) conducting principal component analysis on the portion of said preselected data correlated with the tissue lesion, (ii) obtaining by principal component analysis a plurality of eigenvectors, (iii) performing analysis of at least the portion of the preselected data by 3TP algorithm labeling to obtain an output of color hue/color intensity coded images with respect to transcapillary transfer constants and extracellular extravascular volume fraction indicative of the at least one type of tissue lesion wherein color intensity reflects changes in signal intensity between the 1st time point (pre-contrast) and the 2nd time point (termed "wash-in rate"), and color hue reflects changes in signal intensity between the 2nd time point and the 3rd time point (termed "wash-out pattern") according to one preselected color for increased signal intensity, a second preselected color for no significant change, and a third preselected color for decrease in signal intensity, and (iv) manipulating the x and y axes of the eigenvectors around their z-axis to determine a median rotated eigenvector base $E_{rot}$ for at least two eigenvectors, one of which correlates with the wash-in rate and the other of which correlates with wash-out pattern of the 3TP algorithm labeling color hue/color intensity coded images; by performing principal component analysis on the first dataset of images according to the algorithm $P_{d,s} = \Gamma E_{rot}^{-1}$ wherein $P_{d,s}$ is the projection of the input data (dataset $\Gamma$) on $E_{rot}$ yielding projection coefficient maps of the rotated at least two eigenvectors and enabling detection of a cancerous lesion by a high intensity appearing in the projection coefficient map of the rotated eigenvector correlated with wash-in rate and by a high intensity appearing in the projection coefficient map of the rotated eigenvector correlated with wash-out pattern, and distinguishing between cancerous lesions and benign lesions by each benign lesion appearing in the projection coefficient map of the rotated eigenvector correlated with wash-out pattern showing as a null or negative intensity; and by outputting the projection coefficient maps of the rotated at least two eigenvectors.

7. A non-transitory computer readable storage according to claim 6 including further non-transitory instructions for programming the computer for converting the obtained first dataset of images to an enhancement dataset of images by normalizing post- contrast images to pre-contrast images using standard definition of enhancement, I(t)–I(0)/1(0), where I(0) and (t) pre-contrast and post-contrast intensity values, respectively, for the same pixel; and for performing principal component analysis using the enhancement dataset of images.

8. A non-transitory computer readable storage according to claim 6 including further non-transitory instructions for programming the computer to use blue as the first color, green as the second color and red as the third color.

* * * * *